United States Patent
Papeo et al.

(10) Patent No.: US 9,073,893 B2
(45) Date of Patent: Jul. 7, 2015

(54) 3-OXO-2,3-DIHYDRO-1H-INDAZOLE-4-CARBOXAMIDE DERIVATIVES AS PARP-1 INHIBITORS

(75) Inventors: Gianluca Mariano Enrico Papeo, Lombardone (IT); Daniela Borghi, Nerviano (IT); Michele Caruso, Milan (IT); Helena Posteri, Travedona Monate (IT); Mikhail Yurievitch Krasavin, Nathan (AU)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 14/233,963

(22) PCT Filed: Jul. 18, 2012

(86) PCT No.: PCT/EP2012/064054
§ 371 (c)(1),
(2), (4) Date: Mar. 26, 2014

(87) PCT Pub. No.: WO2013/014038
PCT Pub. Date: Jan. 31, 2013

(65) Prior Publication Data
US 2014/0235675 A1    Aug. 21, 2014

(30) Foreign Application Priority Data

Jul. 26, 2011  (EP) ..................... 11175355
May 9, 2012   (EP) ..................... 12167336

(51) Int. Cl.
| | | |
|---|---|---|
| C07D 401/04 | (2006.01) |
| C07D 401/14 | (2006.01) |
| C07D 405/14 | (2006.01) |
| C07D 401/10 | (2006.01) |
| C07D 403/04 | (2006.01) |
| C07D 409/14 | (2006.01) |
| A61K 31/4188 | (2006.01) |
| A61K 31/454 | (2006.01) |

(52) U.S. Cl.
CPC .......... *C07D 401/04* (2013.01); *C07D 401/14* (2013.01); *C07D 405/14* (2013.01); *C07D 401/10* (2013.01); *C07D 403/04* (2013.01); *C07D 409/14* (2013.01); *A61K 31/4188* (2013.01); *A61K 31/454* (2013.01)

(58) Field of Classification Search
None
See application file for complete search history.

(56) References Cited

FOREIGN PATENT DOCUMENTS

| EP | 0 355 970 A1 | 2/1990 |
|---|---|---|
| WO | WO 02/100833 A1 | 12/2002 |
| WO | WO 2007/041357 A1 | 4/2007 |
| WO | WO 2008/084261 A1 | 7/2008 |
| WO | WO 2008/141385 A1 | 11/2008 |
| WO | WO 2010/133647 A1 | 11/2010 |
| WO | WO 2011/006803 A1 | 1/2011 |

OTHER PUBLICATIONS

Fujimoto T. et al., "Discovery of a Tetrahydropyrimidin-2(1H)-One Derivative (TAK-442) as a Potent, Selective, and Orally Active Factor XA Inhibitor", Journal of Medicinal Chemistry 53:3517-3531 (2010).
Simeoni M. et al., "Predictive Pharmacokinetic-Pharmacodynamic Modeling of Tumor Growth Kinetics in Xenograft Models After Administration of Anticancer Agents", Cancer Research 64:1094-1101 (Feb. 1, 2004).
Zhao Z. et al., "Synthesis and Evaluation of Novel Pyrazolidinone Analogs of PGE2 as EP2 and EP4 Receptors Agonists", Bioorganic & Medicinal Chemistry Letters 17:6572-6575 (2007).
Zhao C. et al., "Synthesis and Activity of N-Acyl Azacyclic Urea HIV-1 Protease Inhibitors With High Potency Against Multiple Drug Resistant Viral Strains", Bioorganic & Medicinal Chemistry Letters 15:5499-5503 (2005).
International Search Report dated Oct. 5, 2012 issued in PCT/EP2012/064054.

*Primary Examiner* — Timothy R Rozof
(74) *Attorney, Agent, or Firm* — Scully, Scott, Murphy & Presser, P.C.

(57) ABSTRACT

There are provided 3-oxo-2,3-dihydro-1H-indazole-4-carboxamide derivatives which selectively inhibit the activity of poly (ADP-ribose) polymerase PARP-1 with respect to poly (ADP-ribose) polymerase PARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

21 Claims, No Drawings

3-OXO-2,3-DIHYDRO-1H-INDAZOLE-4-CARBOXAMIDE DERIVATIVES AS PARP-1 INHIBITORS

The present invention provides 3-oxo-2,3-dihydro-1H-indazole-4-carboxamide derivatives which selectively inhibit the activity of poly (ADP-ribose) polymerase PARP-1 with respect to poly (ADP-ribose) polymerase PARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

Poly (ADP-ribose) polymerases belong to a family of 18 members that catalyze the addition of ADP-ribose units to DNA or different acceptor proteins, which affect cellular processes as diverse as replication, transcription, differentiation, gene regulation, protein degradation and spindle maintenance. PARP-1 and PARP-2 are the only enzymes among the PARPs that are activated by DNA damage and are involved in DNA repair.

PARP-1 is a nuclear protein consisting of three domains: the N-terminal DNA-binding domain containing two zinc fingers, the auto modification domain, and the C-terminal catalytic domain. PARP-1 binds through the zinc-finger domain to DNA single strand breaks (SSB), cleaves NAD+, and attaches multiple ADP-ribose units to target proteins such as histones and various DNA repair enzymes. This results in a highly negatively charged target, which in turn leads to the unwinding and repair of the damaged DNA through the base excision repair pathway. In knock out mouse models, deletion of PARP-1 impairs DNA repair but it is not embryonic lethal. Double knock out PARP-1 and PARP-2 mice instead die during early embryogenesis, suggesting that the two enzymes display not completely overlapping functions. Enhanced PARP-1 expression and/or activity have been shown in different tumor cell lines, including malignant lymphomas, hepatocellular carcinoma, cervical carcinoma, colorectal carcinoma, leukemia. This may allow tumor cells to withstand genotoxic stress and increase their resistance to DNA-damaging agents. As a consequence, inhibition of PARP-1 through small molecules has been shown to sensitize tumor cells to cytotoxic therapy (e.g. temozolomide, platinums, topoisomerase inhibitors and radiation). A significant window seems to exist between the ability of a PARP inhibitor to potentiate therapeutic benefits and undesirable side effects. Whereas the therapeutic use of PARP inhibitors in combination with DNA damaging agents is not novel, the use of these agents as monotherapy, in particular tumor genetic backgrounds deficient in the homologous recombination DNA repair, represents a new approach. Individuals with heterozygous germ line mutations in either the BRCA-1 or BRCA-2 homologous recombination repair genes exhibit high life time risks of developing breast and other cancers. Tumors arising in mutation carriers have generally lost the wild type allele and do not express functional BRCA-1 and BRCA-2 proteins.

Therefore, loss of these two proteins leads to a tumor-specific dysfunction in the repair of double strand breaks by homologous recombination. It is known that when PARP-1 is inhibited, base excision repair is reduced and single strand breaks that are generated during the normal cell cycle persist. It has also been established that replication forks that encounter an unrepaired break can form double strand breaks which are normally repaired by homologous recombination. Tumor cells that are deficient in homologous recombination repair such as BRCA-1 and BRCA-2 mutants are therefore highly sensitive to PARP inhibition compared with wild-type cells. This is in line with the concept of synthetic lethality, in which the two pathway defects alone are innocuous but combined become lethal: PARP inhibitors may be more effective in patients with tumors with specific DNA repair defects without affecting normal heterozygous tissues. Putative patient population includes, besides BRCA mutants that represent the majority of hereditary breast and ovarian cancer, also a substantial fraction of sporadic cancers with defects in homologous recombination repair, a phenomenon termed "BRCAness". For example, methylation of the promoters of the BRCA-1 or FANCF genes and amplification of the EMSY gene, which encodes a BRCA-2 interacting protein. By extending the rational of synthetic lethality of PARP and BRCA-1 and BRCA-2, it is likely that deficiencies in any gene that is not redundant in double strand break repair should be sensitive to PARP inhibition. For example, ATM deficiency, found in patients with T-cell prolymphocytic leukemia and B-cell chronic lymphocytic leukemia and breast cancer and CHK2 germ line mutations identified in sarcoma, breast cancer, ovarian cancer and brain tumors, have also been shown to be synthetically lethal in combination with PARP deficiency as well as deficiencies in other known HR pathway proteins (including RAD51, DSS1, RAD54, RPA1, NBS1, ATR, CHK1, CHK2, FANCD2, FANCA, and FANCC).

Mutations in FANCC and FANCG have been shown in pancreatic cancer. Methylation of FANCF promoter has been found in ovarian, breast, cervical, lung carcinomas. The first clinical evidence that BRCA-mutated cancer may be sensitive to PARP inhibitor monotherapy comes from the preliminary data for the phase I trial of the oral, small molecule PARP inhibitor Olaparib. In an enriched phase I population for BRCA mutation carriers, partial responses were seen in 4 out of 10 ovarian cancer patients with confirmed BRCA-1 mutations. Other PARP inhibitors, such as Rucaparib and Veliparib are currently known to be in phase II clinical trials both in combination with DNA damaging agents and as single agent in BRCA deficient tumors. Early indications are that these therapies show low toxicity. Anyway compounds with high selectivity on PARP-1 are expected to show even less toxicity in view of a chronic treatment schedule.

PARP-1 has also been implicated in angiogenesis. In particular, PARP-1 inhibition seems to result in decreased accumulation of the transcription hypoxia-inducible factor 1α, an important regulator of tumor cell adaptation to hypoxia.

Pro-inflammatory stimuli trigger the release of pro-inflammatory mediators that induce the production of peroxynitrate and hydroxyl radicals, which in turn yield to DNA single strand breakage with consequent activation of PARP-1. Over activation of PARP-1 results in depletion of NAD+ and energy stores, culminating in cell dysfunction and necrosis. This cellular suicide mechanism has been implicated in the pathomechanism of stroke, myocardial ischemia, diabetes, diabetes-associated cardiovascular dysfunction, shock, traumatic central nervous system injury, arthritis, colitis, allergic encephalomyelitis and various other forms of inflammation. Of special interest is the enhancement by PARP-1 of nuclear factor kB-mediated transcription, which plays a central role in the expression of inflammatory cytokines, chemokines and inflammatory mediators.

WO 2002/100833 in the name of Dainippon Sumitomo Pharma describes indazole derivatives useful for treating and preventing e.g. urinary incontinence and hypertension.

WO 2008/141385 in the name of Biota Scientific Management describes indazol-3-one derivatives useful for treating HCV infections.

EP 355970 in the name of ICI-Pharma describes 4-carbamoylindazol-3-one derivatives useful for treating inflammatory allergic diseases.

The present invention provides novel 3-oxo-2,3-dihydro-1H-indazole-4-carboxamide derivatives of formula (I) which are selective PARP-1 inhibitors with respect to PARP-2 and are thus useful in the therapy of cancer, cardiovascular diseases, nervous system injury and inflammation.

Accordingly, a first object of the present invention is to provide a compound of formula (I):

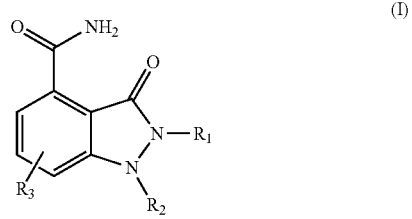

wherein $R_1$ is an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl and heteroaryl;

$R_2$ is hydrogen, $COR_4$ or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl and heteroaryl;

$R_3$ is hydrogen, halogen, cyano, nitro, $NHCOR_4$, $COR_4$, $NR_5R_6$, $NR_5COR_4$, $OR_7$, $SR_7$, $SOR_{10}$, $SO_2R_{10}$, $NHSOR_{10}$, $NHSO_2R_{10}$, or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl;

$R_4$ is hydrogen, $NR_5R_7$, $OR_7$, $SR_7$, or an optionally substituted group selected from linear or branched $C_1$-$C_6$ alkyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl;

$R_5$ and $R_6$ are independently hydrogen, or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl, or $R_5$ and $R_6$, taken together with the nitrogen to which they are bonded, form an optionally substituted heterocyclyl group;

$R_7$ is hydrogen, $COR_5$, $SOR_{10}$, $SO_2R_{10}$ or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl, $R_8O$—$C_1$-$C_6$ alkyl, heterocyclyl-$C_1$-$C_6$ alkyl, aryl-$C_1$-$C_6$alkyl and heteroaryl-$C_1$-$C_6$alkyl, wherein $R_5$ is as defined above;

$R_8$ and $R_9$ are independently hydrogen, $COR_4$ or an optionally substituted group selected from linear or branched $C_1$-$C_6$ alkyl, $C_2$-$C_6$ alkenyl, $C_2$-$C_6$alkynyl, $C_3$-$C_7$ cycloalkyl, heterocyclyl, aryl and heteroaryl, or $R_8$ and $R_9$, taken together with the nitrogen to which they are bonded, form an optionally substituted heterocyclyl group, wherein $R_4$ is as defined above;

$R_{10}$ is hydrogen, $NR_5R_6$, $OR_7$ or an optionally substituted group selected from linear or branched $C_1$-$C_6$ alkyl, $C_2$-$C_6$ alkenyl, $C_2$-$C_6$alkynyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl, wherein $R_5$, $R_6$, $R_7$, $R_8$ and $R_9$ are as defined above;

or a pharmaceutically acceptable salt thereof.

The present invention also provides methods of synthesizing 3-oxo-2,3-dihydro-1H-indazole-4-carboxamide derivatives of formula (I) prepared through a process consisting of standard synthetic transformations.

The present invention also provides a method for treating diseases mediated by PARP-1 protein which comprises administering to a mammal in need thereof, preferably a human, an effective amount of a compound of formula (I), as defined above.

A preferred method of the present invention is to treat a disease mediated by PARP-1 protein selected from the group consisting of cancer, cardiovascular diseases, nervous system injury and inflammation.

Another preferred method of the present invention is to treat specific types of cancer including but not limited to: carcinomas, such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

In addition, the method of the present invention also provides tumor angiogenesis and metastasis inhibition.

Another preferred method of the present invention is to treat specific types of cardiovascular diseases including but not limited to: myocardial reperfusion injury, cardiomyopathy, diabetic cardiovascular dysfunction.

Another preferred method of the present invention is to treat specific types of central nervous system injury including but not limited to: stroke, brain injury and neurodegenerative disorders.

Another preferred method of the present invention is to treat specific types of inflammation diseases including, but not limited to, colitis, arthritis and uveitis.

The present invention also provides an in vitro method for selectively inhibiting PARP-1 protein activity which comprises contacting the said protein with an effective amount of a compound of formula (I).

The present invention further provides a method of treatment comprising a compound of formula (I) in combination with radiation therapy or chemotherapy regimen for simultaneous, separate or sequential use in anticancer therapy.

The present invention also provides a pharmaceutical composition comprising a therapeutically effective amount of a compound of formula (I) or a pharmaceutically acceptable salt thereof, as defined above, and at least one pharmaceutically acceptable excipient, carrier or diluent.

In addition to a compound of formula (I), the pharmaceutical composition of the present invention may further comprise one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like. Preferably, the chemotherapeutic agent is an alkylating agent. Even more preferably, the alkylating agent is temozolomide.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy. Preferably, the chemotherapeutic agent is an alkylating agent. Even more preferably, the alkylating agent is temozolomide.

Moreover, the invention provides a compound of formula (I) or a pharmaceutically acceptable salt thereof, as defined above, for use as a medicament, preferably as a medicament with anticancer activity.

In yet another aspect, the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

The compounds of formula (I) may have one or more asymmetric centers, and may therefore exist as individual optical isomers or racemic mixtures or diastereoisomers. Accordingly, all the possible isomers, and their mixtures of the compounds of formula (I) are within the scope of the present invention. As stated above, salts of the compounds of formula (I) are also within the scope of the present invention.

Unless otherwise specified, when referring to the compounds of formula (I) per se as well as to any pharmaceutical composition thereof or to any therapeutic treatment comprising them, the present invention includes all of the isomers, tautomers, hydrates, solvates, N-oxides and pharmaceutically acceptable salts of the compounds of this invention.

If a chiral center or another form of an isomeric center is present in a compound of the present invention, all forms of such isomer or isomers, including enantiomers and diastereoisomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

With the term "halogen" we intend a fluorine, chlorine, bromine or iodine.

With the term "cyano" we intend a —CN residue.

With the term "nitro" we intend a —$NO_2$ group.

With the term "linear or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_2$-$C_6$ alkenyl" we intend an aliphatic $C_2$-$C_6$ hydrocarbon chain containing at least one carbon-carbon double bond and which can be linear or branched. Representative examples include, but are not limited to, ethenyl, 1-propenyl, 2-propenyl, 1- or 2-butenyl, and the like.

With the term "$C_2$-$C_6$ alkynyl" we intend an aliphatic $C_2$-$C_6$ hydrocarbon chain containing at least one carbon-carbon triple bond and which can be linear or branched. Representative examples include, but are not limited to, ethynyl, 1-propynyl, 2-propynyl, 1- or 2-butynyl, and the like.

With the term "$C_3$-$C_7$ cycloalkyl" we intend, unless otherwise provided, a 3- to 7-membered all-carbon monocyclic ring, which may contain one or more double bonds but does not have a completely conjugated 7-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated 7-electron bond system. Non-limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Non limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

According to the present invention and unless otherwise provided, any of the above $R_1$-$R_3$ groups may be optionally substituted, in any of their free positions, by one or more groups, for instance 1 to 6 groups, independently selected from: halogen, nitro, oxo groups (=O), cyano, $C_1$-$C_6$ alkyl, polyfluorinated alkyl, polyfluorinated alkoxy, $C_2$-$C_6$ alkenyl, $C_2$-$C_6$ alkynyl, hydroxyalkyl, aryl, arylalkyl, heteroaryl, heteroarylalkyl, heterocyclyl, heterocyclylalkyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl-alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term "polyfluorinated alkyl" or "polyfluorinated alkoxy" we intend any of the above linear or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxyalkyl" we intend any of the above $C_1$-$C_6$ alkyl, bearing a hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

In particular, in the above definition, "optionally substituted" means that the group may be substituted with one or more substituents independently selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl or heteroaryl-$C_1$-$C_6$ alkyl group, halogen, cyano, nitro, $NHCOR_4$, $COR_4$, $NR_5R_6$, $NR_5COR_4$, $OR_7$, oxo (=O), $SR_7$, $SOR_{10}$, $SO_2R_{10}$, $NHSOR_{10}$, $NHSO_2R_{10}$, $R_8R_9N$—$C_1$-$C_6$ alkyl, $R_8O$—$C_1$-$C_6$ alkyl group.

All those substituents may be optionally further substituted with one or more substituents independently selected from halogen, $C_1$-$C_6$ alkyl, aryl or heterocyclyl group, $NHCOR_4$, $NR_5R_6$, $NR_5COR_4$, $OR_7$, oxo (=O), $SR_7$, $R_8R_9N$—$C_1$-$C_6$ alkyl, $R_8O$—$C_1$-$C_6$ alkyl, wherein $R_4$, $R_5$, $R_6$, $R_7$, $R_8$, $R_9$ and $R_{10}$ are as defined above.

The term "pharmaceutically acceptable salt" of compounds of formula (I) refers to those salts that retain the biological effectiveness and properties of the parent compound, therefore pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, (D) or (L) lactic, oxalic, ascorbic, fumaric, malonic, malic, maleic, tartaric, citric, benzoic, cinnamic, mandelic, methanesulphonic, ethanesulfonic, p-toluenesulfonic, isethionic, succinic and salicylic acid.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines, preferably methylamine, ethylamine, diethylamine, triethylamine, piperidine and the like.

In a first preferred embodiment, compounds of general formula (I) are characterized in that $R_1$ is an optionally substituted group selected from linear or branched $C_1$-$C_6$ alkyl, $C_3$-$C_7$ cycloalkyl, heterocyclyl, aryl and heteroaryl, the optional substituents being one or more halogen, cyano, $NHCOR_4$, $COR_4$, $NR_5R_6$, $NR_5COR_4$, $OR_7$, oxo (=O) or an optionally substituted group selected from linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl, heteroaryl-$C_1$-$C_6$ alkyl, $R_8R_9N$—$C_1$-$C_6$ alkyl and $R_8O$—$C_1$-$C_6$ alkyl, the optional further substituents being one or more halogen, $NHCOR_4$, $NR_5R_6$, $NR_5COR_4$, $OR_7$, oxo (=O), $SR_7$, or an optionally substituted group selected from linear or branched $C_1$-$C_6$ alkyl, aryl, heterocyclyl, $R_8R_9N$—$C_1$-$C_6$ alkyl and $R_8O$—$C_1$-$C_6$ alkyl; and $R_2$, $R_3$, $R_4$, $R_5$, $R_6$, $R_7$, $R_8$ and $R_9$ are as defined above.

In a second preferred embodiment, compounds of general formula (I) are characterized in that $R_1$ is an optionally substituted group selected from $C_3$-$C_7$ cycloalkyl, heterocyclyl, aryl and heteroaryl, the optional substituents being one or more halogen atom, cyano, $NHCOR_4$, $COR_4$, $NR_5R_6$, $NR_5COR_4$, $OR_7$, oxo (=O) or an optionally substituted group selected from linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl, heteroaryl-$C_1$-$C_6$ alkyl, $R_8R_9N$—$C_1$-$C_6$ alkyl and $R_8O$—$C_1$-$C_6$ alkyl, the optional further substituents being one or more halogen, $NHCOR_4$, $NR_5R_6$, $NR_5COR_4$, $OR_7$, oxo (=O), $SR_7$ or an optionally substituted group selected from linear or branched $C_1$-$C_6$ alkyl, aryl, heterocyclyl, $R_8R_9N$—$C_1$-$C_6$ alkyl and $R_8O$—$C_1$-$C_6$ alkyl;

$R_2$ is hydrogen, $COR_4$ or an optionally substituted group selected from linear or branched $C_1$-$C_6$ alkyl, $C_3$-$C_7$ cycloalkyl, heterocyclyl, aryl and heteroaryl;

and $R_3$, $R_4$, $R_5$, $R_6$, $R_7$, $R_8$ and $R_9$ are as defined above.

In a third preferred embodiment, compounds of general formula (I) are characterized in that $R_2$ is hydrogen or an optionally substituted group selected from linear or branched $C_1$-$C_6$ alkyl, $C_3$-$C_7$ cycloalkyl, heterocyclyl, aryl and heteroaryl;

$R_3$ is hydrogen, halogen, cyano, nitro, $NHCOR_4$, $NR_5R_6$, $NR_5COR_4$, $OR_7$, or an optionally substituted group selected from linear or branched $C_1$-$C_6$alkyl, $R_8R_9N$—$C_1$-$C_6$ alkyl and $R_8O$—$C_1$-$C_6$ alkyl;

and $R_1$, $R_4$, $R_5$, $R_6$, $R_7$, $R_8$, and $R_9$ are as defined above.

In a fourth preferred embodiment, compounds of general formula (I) are characterized in that $R_3$ is hydrogen, halogen, $NHCOR_4$, $NR_5R_6$, $NR_5COR_4$, $OR_7$ or an optionally substituted group selected from linear or branched $C_1$-$C_6$ alkyl, $R_8R_9N$—$C_1$-$C_6$ alkyl and $R_8O$—$C_1$-$C_6$ alkyl;

and $R_1$, $R_2$, $R_4$, $R_5$, $R_6$, $R_7$, $R_8$, and $R_9$ are as defined above.

In a fifth preferred embodiment, compounds of general formula (I) are characterized in that $R_1$ is an optionally substituted group selected from heterocyclyl, aryl and heteroaryl, the optional substituents being, one or more $COR_4$ or an optionally further substituted group selected from linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl and heteroaryl-$C_1$-$C_6$ alkyl, the optional further substituents being one or more halogen atom, $OR_7$, oxo(=O) or an optionally substituted group selected from $C_1$-$C_6$alkyl, aryl, heterocyclyl and $R_8O$—$C_1$-$C_6$ alkyl;

$R_2$ is hydrogen or a $C_1$-$C_6$alkyl group;

$R_3$ is hydrogen or halogen;

$R_4$ is $OR_7$, $R_7$ is hydrogen, optionally substituted $C_1$-$C_6$alkyl or aryl-$C_1$-$C_6$alkyl group, substituents being one or more halogen;

$R_8$ is hydrogen;

and $R_5$, $R_6$ and $R_9$ are as defined above.

In a sixth preferred embodiment, compounds of general formula (I) are characterized in that $R_1$ is an optionally substituted piperidinyl or phenyl group, the optional substituents being, one or more, $COR_4$ or an optionally further substituted group selected from methyl, ethyl, propyl, cyclohexyl, cyclopentyl, cyclobutyl, morpholinyl, piperazinyl, pyrazolyl, cyclohexyl-methyl, cyclohexenyl-methyl, piperidinyl-methyl, benzyl, pyridyl-methyl, pyrrolyl-methyl, pyrazolyl-methyl, imidazolyl-methyl, thienyl-methyl, indolyl-methyl, thiazolyl-methyl and furyl-methyl, the optional further substituents being one or more bromine, fluorine, chlorine, isopropyl, methyl, phenyl, morpholinyl, piperidinyl, hydroxymethyl, $OR_7$, or oxo (=O);

$R_2$ is hydrogen or a methyl group;
$R_3$ is hydrogen or fluorine;
$R_4$ is $OR_7$,
$R_7$ is hydrogen, an optionally substituted methyl, tert-butyl or benzyl group, the substituents being one or more fluorine; and $R_4$, $R_5$, $R_6$, $R_8$ and $R_9$ are as defined above.

Specific compounds (cpd) of the present invention or salts thereof, are listed below:

1. 3-oxo-2-(piperidin-4-yl)-2,3-dihydro-1H-indazole-4-carboxamide,
2. 2-(1-cyclopentylpiperidin-4-yl)-3-oxo-2,3-dihydro-1H-indazole-4-carboxamide,
3. 2-(1-cyclohexylpiperidin-4-yl)-3-oxo-2,3-dihydro-1H-indazole-4-carboxamide,
4. 2-[1-(4,4-difluorocyclohexyl)piperidin-4-yl]-3-oxo-2,3-dihydro-1H-indazole-4-carboxamide,
5. 2-(1-cyclohexylpiperidin-4-yl)-1-methyl-3-oxo-2,3-dihydro-1H-indazole-4-carboxamide,
6. 2-[1-(4,4-difluorocyclohexyl)piperidin-4-yl]-1-methyl-3-oxo-2,3-dihydro-1H-indazole-4-carboxamide,
7. 2-(1-cyclopentylpiperidin-4-yl)-1-methyl-3-oxo-2,3-dihydro-1H-indazole-4-carboxamide,
8. 2-(1-methylpiperidin-4yl)-3-oxo-2,3-dihydro-1H-indazole-4-carboxamide,
9. 1-methyl-3-oxo-2-(piperidin-4-yl)-2,3-dihydro-1H-indazole-4-carboxamide,
10. 1-methyl-2-(1-methylpiperidin-4-yl)-3-oxo-2,3-dihydro-1H-indazole-4-carboxamide,
11. 2-(1-ethylpiperidin-4-yl)-3-oxo-2,3-dihydro-1H-indazole-4-carboxamide,
12. 3-oxo-2-(1-propylpiperidin-4-yl)-2,3-dihydro-1H-indazole-4-carboxamide,
13. 2-(1-ethylpiperidin-4-yl)-1-methyl-3-oxo-2,3-dihydro-1H-indazole-4-carboxamide,
14. 1-methyl-3-oxo-2-[1-(propan-2-yl)piperidin-4-yl]-2,3-dihydro-1H-indazole-4-carboxamide,
15. 3-oxo-2-[1-(propan-2-yl)piperidin-4-yl]-2,3-dihydro-1H-indazole-4-carboxamide,
16. 2-(1-cyclobutylpiperidin-4-yl)-3-oxo-2,3-dihydro-1H-indazole-4-carboxamide,
17. 2-(1-cyclobutylpiperidin-4-yl)-6-fluoro-3-oxo-2,3-dihydro-1H-indazole-4-carboxamide,
18. 2-(1-cyclobutylpiperidin-4-yl)-1-methyl-3-oxo-2,3-dihydro-1H-indazole-4-carboxamide,
19. 2-(1-cyclobutylpiperidin-4-yl)-6-fluoro-1-methyl-3-oxo-2,3-dihydro-1H-indazole-4-carboxamide,
20. 6-fluoro-3-oxo-2-(piperidin-4-yl)-2,3-dihydro-1H-indazole-4-carboxamide,
21. 6-fluoro-1-methyl-3-oxo-2-(piperidin-4-yl)-2,3-dihydro-1H-indazole-4-carboxamide,
22. 2-(1-cyclohexylpiperidin-4-yl)-6-fluoro-1-methyl-3-oxo-2,3-dihydro-1H-indazole-4-carboxamide,
23. 2-(1-cyclohexylpiperidin-4-yl)-6-fluoro-3-oxo-2,3-dihydro-1H-indazole-4-carboxamide,
24. 2-[1-(4,4-difluorocyclohexyl)piperidin-4-yl]-6-fluoro-1-methyl-3-oxo-2,3-dihydro-1H-indazole-4-carboxamide,
25. 2-[1-(4,4-dichlorocyclohexyl)piperidin-4-yl]-1-methyl-3-oxo-2,3-dihydro-1H-indazole-4-carboxamide,
26. 6-chloro-2-(1-cyclohexylpiperidin-4-yl)-1-methyl-3-oxo-2,3-dihydro-1H-indazole-4-carboxamide,
27. 2-(1-cyclohexylazetidin-3-yl)-3-oxo-2,3-dihydro-1H-indazole-4-carboxamide,
28. 2-(1-cyclohexylazetidin-3-yl)-1-methyl-3-oxo-2,3-dihydro-1H-indazole-4-carboxamide,
29. 6-chloro-2-(1-cyclohexylpiperidin-4-yl)-3-oxo-2,3-dihydro-1H-indazole-4-carboxamide,
30. 2-(1-cyclohexylazetidin-3-yl)-6-fluoro-1-methyl-3-oxo-2,3-dihydro-1H-indazole-4-carboxamide,
31. 2-[1-(cyclohexylmethyl)piperidin-4-yl]-3-oxo-2,3-dihydro-1H-indazole-4-carboxamide,
32. 2-(1-benzylpiperidin-4-yl)-3-oxo-2,3-dihydro-1H-indazole-4-carboxamide,
33. 2-[1-(cyclohexylmethyl)piperidin-4-yl]-1-methyl-3-oxo-2,3-dihydro-1H-indazole-4-carboxamide,
34. 2-(1-benzylpiperidin-4-yl)-1-methyl-3-oxo-2,3-dihydro-1H-indazole-4-carboxamide,
35. 3-oxo-2-(1-phenylpiperidin-4-yl)-2,3-dihydro-1H-indazole-4-carboxamide,
36. 1-methyl-3-oxo-2-(1-phenylpiperidin-4-yl)-2,3-dihydro-1H-indazole-4-carboxamide,
37. 6-fluoro-1-methyl-3-oxo-2-[4-(piperidin-4-yl)phenyl]-2,3-dihydro-1H-indazole-4-carboxamide,
38. 3-oxo-2-[4-(piperidin-4-yl)phenyl]-2,3-dihydro-1H-indazole-4-carboxamide,
39. 1-methyl-3-oxo-2-[4-(piperidin-4-yl)phenyl]-2,3-dihydro-1H-indazole-4-carboxamide,
40. 6-fluoro-1-methyl-3-oxo-2-(1-phenylpiperidin-4-yl)-2,3-dihydro-1H-indazole-4-carboxamide,
41. 3-oxo-2-[1-(thiophen-3-ylmethyl)piperidin-4-yl]-2,3-dihydro-1H-indazole-4-carboxamide,
42. 3-oxo-2-[1-(1H-pyrrol-3-ylmethyl)piperidin-4-yl]-2,3-dihydro-1H-indazole-4-carboxamide,
43. 6-fluoro-1-methyl-3-oxo-2-[1-(thiophen-3-ylmethyl)piperidin-4-yl]-2,3-dihydro-1H-indazole-4-carboxamide,
44. 1-methyl-3-oxo-2-[1-(1H-pyrrol-3-ylmethyl)piperidin-4-yl]-2,3-dihydro-1H-indazole-4-carboxamide,
45. 2-[1-(furan-3-ylmethyl)piperidin-4-yl]-1-methyl-3-oxo-2,3-dihydro-1H-indazole-4-carboxamide,
46. 3-oxo-2-[1-(pyridin-4-yl)piperidin-4-yl]-2,3-dihydro-1H-indazole-4-carboxamide,
47. 2-[1-(furan-3-ylmethyl)piperidin-4-yl]-3-oxo-2,3-dihydro-1H-indazole-4-carboxamide,
48. 1-methyl-3-oxo-2-[1-(1H-pyrrol-2-ylmethyl)piperidin-4-yl]-2,3-dihydro-1H-indazole-4-carboxamide,
49. 3-oxo-2-[1-(pyridin-3-yl)piperidin-4-yl]-2,3-dihydro-1H-indazole-4-carboxamide,
50. 1-methyl-3-oxo-2-[1-(pyridin-4-yl)piperidin-4-yl]-2,3-dihydro-1H-indazole-4-carboxamide,
51. 1-methyl-3-oxo-2-[1-(pyridin-3-yl)piperidin-4-yl]-2,3-dihydro-1H-indazole-4-carboxamide,
52. 6-fluoro-1-methyl-3-oxo-2-[1-(pyridin-4-yl)piperidin-4-yl]-2,3-dihydro-1H-indazole-4-carboxamide,
53. 6-fluoro-1-methyl-3-oxo-2-[1-(pyridin-3-yl)piperidin-4-yl]-2,3-dihydro-1H-indazole-4-carboxamide,
54. 3-oxo-2-[4-(pyridin-4-yl)phenyl]-2,3-dihydro-1H-indazole-4-carboxamide,
55. 1-ethyl-3-oxo-2-(piperidin-4-yl)-2,3-dihydro-1H-indazole-4-carboxamide,
56. 2-(1-cyclohexylpiperidin-4-yl)-1-ethyl-3-oxo-2,3-dihydro-1H-indazole-4-carboxamide,
57. 1-methyl-3-oxo-2-[4-(pyridin-4-yl)phenyl]-2,3-dihydro-1H-indazole-4-carboxamide,
58. 1-ethyl-6-fluoro-3-oxo-2-(piperidin-4-yl)-2,3-dihydro-1H-indazole-4-carboxamide, 59. 3-oxo-2-[4-(pyridin-3-yl)phenyl]-2,3-dihydro-1H-indazole-4-carboxamide,
60. 6-fluoro-3-oxo-2-[4-(pyridin-3-yl)phenyl]-2,3-dihydro-1H-indazole-4-carboxamide,
61. 6-fluoro-1-methyl-3-oxo-2-[4-(pyridin-3-yl)phenyl]-2,3-dihydro-1H-indazole-4-carboxamide,
62. 3-oxo-2-[1-(thiophen-2-ylmethyl)piperidin-4-yl]-2,3-dihydro-1H-indazole-4-carboxamide,
63. 1-methyl-3-oxo-2-[1-(thiophen-2-ylmethyl)piperidin-4-yl]-2,3-dihydro-1H-indazole-4-carboxamide,
64. 2-[1-(cyclohex-3-en-1-ylmethyl)piperidin-4-yl]-3-oxo-2,3-dihydro-1H-indazole-4-carboxamide,
65. 2-[1-(cyclohex-3-en-1-ylmethyl)piperidin-4-yl]-1-methyl-3-oxo-2,3-dihydro-1H-indazole-4-carboxamide,
66. 2-[1-(furan-2-ylmethyl)piperidin-4-yl]-3-oxo-2,3-dihydro-1H-indazole-4-carboxamide and
67. 2-[1-(furan-2-ylmethyl)piperidin-4-yl]-1-methyl-3-oxo-2,3-dihydro-1H-indazole-4-carboxamide.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protective groups may be necessary to prevent certain functional groups from undergoing undesired reactions. Suitable protective groups for various functional groups as well as suitable conditions for protecting and deprotecting particular functional groups are well known in the art. For example, numerous protective groups are described in Greene, Theodora W. and Wuts, Peter G. M.—Protective Groups in Organic Synthesis, Third Edition, John Wiley & Sons Inc., New York (N.Y.), 1999, and references cited therein.

Scheme 1 reported below shows the preparation of a compound of formula (I) as defined above.

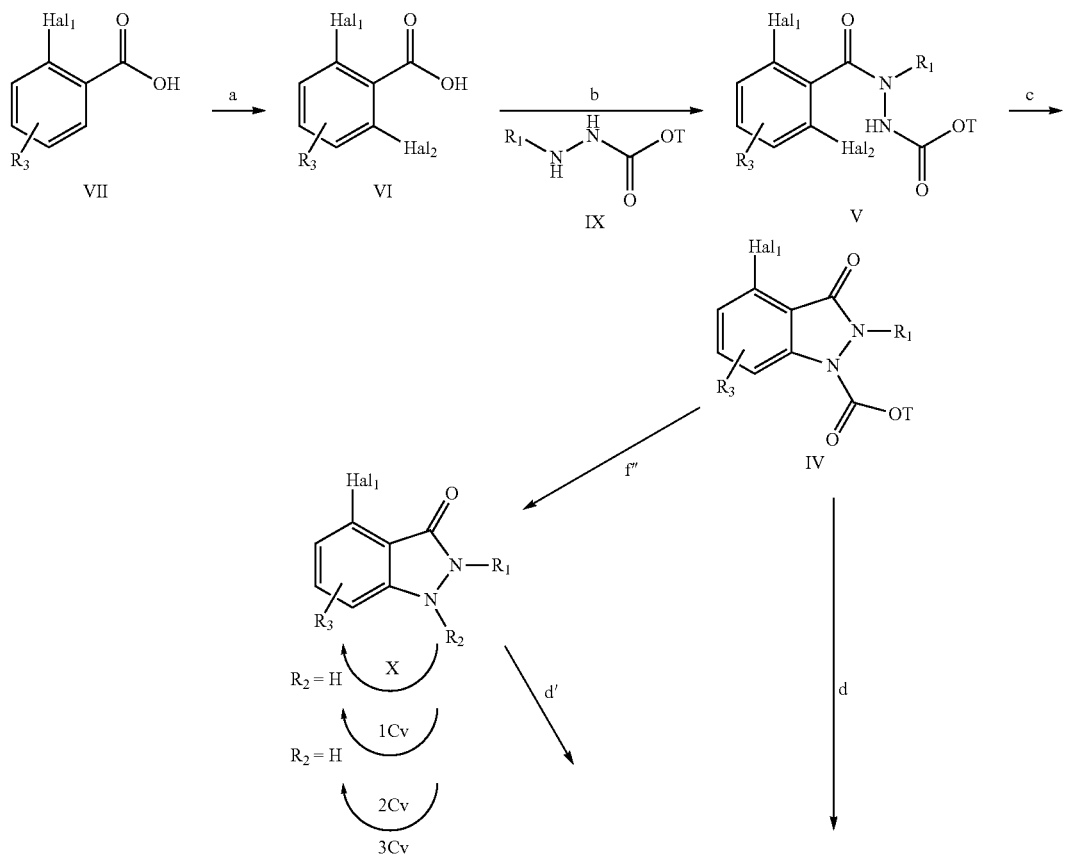

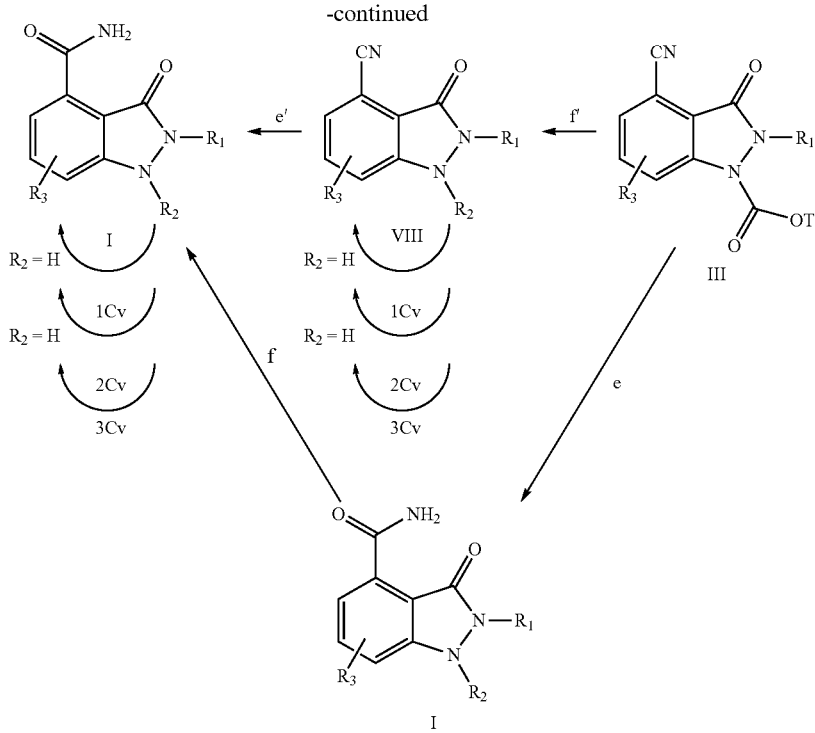

Wherein Hal$_1$ is halogen such as Cl, Br, I; Hal$_2$ is halogen such as Cl, Br, I, different from Hal$_1$;

T is linear or branched C$_1$-C$_6$ alkyl or aryl C$_1$-C$_6$ alkyl group; and R$_1$, R$_2$ and R$_3$ are as defined above.

Accordingly, a process of the present invention comprises the following sequence of steps:

Step a) halogenating a compound of formula (VII):

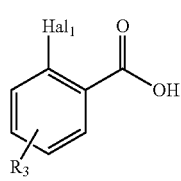

VII wherein Hal$_1$ is halogen such as Cl, Br, I and R$_3$ is as defined above;

Step b) coupling the resultant compound of formula (VI):

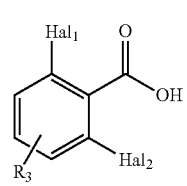

VI wherein Hal$_2$ is halogen such as Cl, Br, I, different from Hal$_1$ and R$_3$ and Hal$_1$ are as defined above, with a suitable hydrazine of formula (IX):

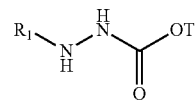

IX wherein T is linear or branched C$_1$-C$_6$ alkyl or aryl C$_1$-C$_6$ alkyl group and R$_1$ is as defined above;

Step c) cyclizing the resultant compound of formula (V):

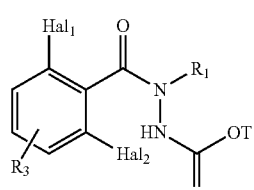

V wherein Hal$_1$, Hal$_2$, T, R$_1$ and R$_3$ are as defined above;
either
Step d) cyano-de-halogenating the resultant compound of formula (IV):

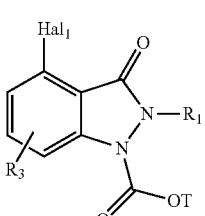

IV wherein Hal$_1$, T, R$_1$ and R$_3$ are as defined above;
or
Step f″) first, removing nitrogen protective group of a compound of formula (IV) as defined above;

Step d') then, cyano-de-halogenating the resultant compound of formula (X):

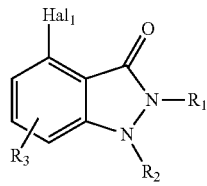

wherein R$_2$ is hydrogen, Hal$_1$, R$_1$ and R$_3$ are as defined above;
either
Step e) first hydrolyzing the compound of formula (III) obtained in step d):

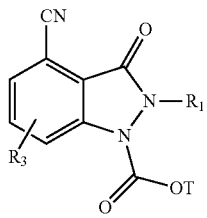

wherein T, R$_1$ and R$_3$ are as defined above;
Step f) then removing nitrogen protective group of the resultant compound of formula (I)

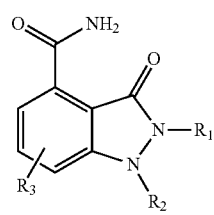

wherein R$_2$ is COR$_4$, R$_4$ is OR$_7$ and R$_7$ is linear or branched C$_1$-C$_6$ alkyl or aryl C$_1$-C$_6$ alkyl; and R$_1$ and R$_3$ are as defined above, to give the corresponding compound of formula (I) wherein R$_2$ is hydrogen, and R$_1$ and R$_3$ are as defined above;
or
Step f') first removing nitrogen protective group of a compound of formula (III) obtained in step d);
Step e') then hydrolyzing the resultant compound of formula (VIII):

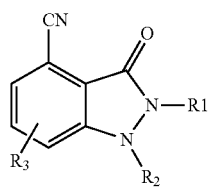

wherein R$_2$ is hydrogen, and R$_1$ and R$_3$ are as defined above, to give a compound of formula (I) wherein R$_2$ is hydrogen, and R$_1$ and R$_3$ are as defined above;

optionally converting a compound of formula (I) into a different compound of formula (I) by known chemical reactions; and/or, if desired, converting a compound of formula (I) into a pharmaceutically acceptable salt thereof or converting a salt into a free compound of formula (I).

Also, an intermediate compound of formula (VIII) or (X) as defined above may be converted into a different compound of formula (VIII) or (X) respectively.

The known chemical reactions for possible conversions of compounds of formula (I), (VIII) or (X) as defined above respectively into a different compound of formula (I), (VIII) or (X) as defined above are for example:

1Cv) deprotection of a compound of formula (I), (VIII) or (IX) as defined above;

2Cv) reductive amination of a compound of formula (I), (VIII) or (X) as defined above;

3Cv) derivatization of a compound of formula (I), (VIII) or (X) as defined above.

All the above processes are analogy processes, which can be carried out according to well known methods and under suitable conditions known in the art.

The synthesis of a compound of formula (I), according to the synthetic processes described above, can be carried out in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

According to step a), a compound of formula (VI) can be obtained by halogenating a compound of formula (VII) in different ways and experimental conditions known in the art. Preferably, this reaction is carried out with tetrabutylammonium bromide and/or iodine in the presence of phenyliodine (III) bis(trifluoracetate) or phenyliodo(III) diacetate as halogen source, in a suitable solvent such as, for instance, N,N-dimethylformamide or dichloroethane, at a temperature ranging from room temperature to reflux and for a time varying from about 1 hour to about 48 hours. The catalyst is usually a metal, most often a palladium derivative such as, for instance, palladium(II) chloride or palladium(II) acetate.

According to step b), a compound of formula (V) can be obtained from a compound of formula (VI) in the presence of a compound of formula (IX) in different ways and experimental conditions known in the art of condensation reactions. A compound of formula (VI) can be reacted with a compound of formula (IX), in the presence of an activating agent such as, for instance, carbonyldiimidazole (CDI), (benzotriazol-1-yloxy)tris(dimethylamino)phosphonium hexafluorophosphate (BOP), 2-(1H-benzotriazol-1yl)-1,1,3,3-tetramethyluronium tetrafluoroborate (TBTU), O-(7-azabenzotriazol-1-yl)-N,N,N',N'-tetramethyluronium hexafluorophosphate (HATU), dicyclohexyl carbodiimide (DCC), diisopropyl carbodiimide, 1-ethyl-3-(3'-dimethylamino)carbodiimide hydrochloric acid salt (EDC), optionally in the presence of hydroxybenzotriazole (HOBt). Preferably, this reaction is carried out in a suitable solvent such as, for instance, N,N-dimethylformamide, N,N-dimethylacetamide, tetrahydrofuran, dichloromethane, 1,4-dioxane, in the presence of a proton scavenger such as, for example, pyridine, triethylamine, N,N-diisopropylethylamine, at a temperature ranging from room temperature to reflux, for a time ranging from about 30 minutes. to about 96 hours. More preferably, a compound of formula (V) can be obtained from a compound of formula (VI) in the presence of a compound of formula (IX) by a two-reaction sequence. First reaction is preferably carried out in the presence of oxalyl chloride, thionyl chloride, phosphorus trichloride or phosphorus pentachloride in a suitable solvent, such as tetrahydrofuran or dichloromethane with or without additive such as, for instance, N,N-dimethylformamide, at a temperature ranging from room temperature to reflux and for a period of time ranging from 10 minutes to about 24 hours. Second step is preferably carried out in the presence of triethylamine, N,N-diisopropylethylamine or N-methylmorpholine, in a suitable solvent such as, for instance, tetrahydrofuran, dichloromethane, N,N-dimethylformamide or N,N-dimethylacetamide, at a temperature ranging from room temperature to reflux and for a period of time ranging from 10 minutes to about 24 hours.

According to step c), the cyclization of a compound of formula (V) to give a compound of formula (IV) can be carried out in different ways and experimental conditions known in the art. Preferably, this reaction is carried out in the presence of a base such as potassium, sodium or cesium carbonate, potassium or sodium hydroxide and reagents such as copper iodide, L-proline or 1,10-phenantroline in a suitable solvent such as, for instance, N,N-dimethylformamide, N,N-dimethylacetamide, dimethylsulfoxide, ethanol, 3,3,3-trifluoroethanol and 1-pentanol, at a temperature ranging from room temperature to reflux and for a period of time ranging from 3 hours to about 48 hours. According to step d) the conversion of a compound of formula (IV) into a compound of formula (III) can be carried out in different ways, according to conventional methods for cyanation reactions. Preferably, this reaction is carried out in the presence of copper(I) or zinc(II) cyanide or potassium hexacyanoferrate (II) as cyano-source in a suitable solvent such as, for instance, methanol, ethanol, tetrahydrofuran, 1,4-dioxane, toluene, xylene, N-methyl-2-pyrrolidone, N,N-dimethylformamide, N,N-dimethylacetamide or a mixture thereof, at a temperature ranging from room temperature to reflux and for a time ranging from about 1 hour to about 96 hours. If a catalyst is required, it is usually a metal, most often a palladium derivative such as, for instance, palladium(II) chloride, palladium (II) acetate, tetrakis(triphenylphosphine)palladium(0) or tris (dibenziyideneacetone)dipalladium(0). If a ligand is required, it is usually a phosphine or a phosphine salt like, for instance, triphenylphosphine, tri-p-tolylphosphine, tricyclohexylphosphine, triisopropylphosphine, tri-tert-butylphosphine, tri-tert-butylphosphine tetrafluoroborate, 1,1'-bis (diphenylphosphino)ferrocene and the like. The reaction can be conducted in the presence of a suitable base such as, for instance, sodium, potassium or cesium carbonate, cesium fluoride. If a reducing environment is required, it could be preferentially obtained with elemental metal such as, for instance, zinc metal.

According to step d') the transformation of a compound of formula (X) into a compound of formula (VIII) can be carried out in different ways and experimental conditions. Preferably it is carried out in a way analogous to that reported for step d).

According to step e), the hydrolysis of a compound of formula (III) to give a compound of formula (I) can be carried out in different ways, according to conventional methods for transforming a cyano group to amide. Preferably, this reaction is carried out in a suitable solvent such as, for instance, methanol, ethanol, n-butanol, 1,4-dioxane, toluene, water, or a mixture thereof, in the presence of a suitable acid or base, such as, for instance, sulfuric acid, hydrochloric acid, methanesulfonic acid, indium chloride, sodium or potassium hydroxide, sodium or potassium carbonate or a suitable reagent such as hydrogen peroxide, sodium perborate or acetaldoxime. Typically, the reaction is carried out at a temperature ranging from room temperature to reflux and for a time ranging from about 1 hour to about 96 hours.

According to step f) a compound of formula (I) can be converted into the corresponding compound of formula (I) by deprotection of the nitrogen atom according to conventional methods enabling the selective hydrolysis of tert-butoxycarbonyl, benzyl, 4-methoxybenzyl, 2,4-dimethoxybenzyl and triphenylmethyl, phenylethyl protective groups. Preferably this reaction is run under acidic conditions, for instance in the presence of an inorganic or organic acid such as hydrochloric, trifluoroacetic or methanesulfonic acid, in a suitable solvent such as dichloromethane, 1,4-dioxane, a lower alcohol, such as methanol or ethanol, at a temperature ranging from room temperature to reflux and for a period of time ranging from about 1 hour to about 48 hours. In alternative, this reaction is carried out under reducing condition, such as, for instance, in the presence of molecular hydrogen and a hydrogenation catalyst in a suitable solvent such as ethanol, methanol, ethyl acetate, or a mixture thereof. The catalyst is usually a metal, most often a palladium derivative such as, for instance, palladium on carbon, palladium hydroxide or palladium black. More preferably, the removal of base-labile protective group can be carried out by using a base such as potassium, sodium or cesium carbonate, potassium or sodium hydroxide, pyridine, triethylamine, N,N-diisopropylethylamine, in a suitable solvent such as methanol, ethanol, at a temperature ranging from room temperature to reflux and for a period of time ranging from about 30 minutes to about 48 hours.

According to step f') the transformation of a compound of formula (III) into a compound of formula (VIII) can be carried out in different ways and experimental conditions. Preferably it is carried out in a way analogous to that reported for step f).

According to step f") the transformation of a compound of formula (IV) into a compound of formula (X) can be carried out in different ways and experimental conditions. Preferably it is carried out in a way analogous to that reported for step f).

According to step e') the transformation of a compound of formula (VIII) into a compound of formula (I) can be carried out in different ways and experimental conditions. Preferably it is carried out in a way analogous to that reported for step e).

According to the conversion described under 1Cv) the deprotection of a compound of formula (I), (VIII) or (X) may be carried out in different ways and experimental conditions. The removal of base-labile protective group can be carried out by using a base such as potassium, sodium or cesium carbonate, potassium or sodium hydroxide, pyridine, triethylamine, N,N-diisopropylethylamine, in a suitable solvent such as methanol, ethanol, at a temperature ranging from room temperature to reflux and for a period of time ranging from about 30 minutes to about 48 hours. Selective hydrolysis of benzyl, 4-methoxybenzyl, 2,4-dimethoxybenzyl and triphenylmethyl, phenylethyl protective groups is run under acidic conditions, for instance in the presence of an inorganic or organic acid such as hydrochloric, trifluoroacetic or methanesulfonic acid, in a suitable solvent such as dichloromethane, 1,4-dioxane, a lower alcohol, such as methanol or ethanol, at a temperature ranging from room temperature to reflux and for a period of time ranging from about 1 hour to about 48 hours. Alternatively, this reaction is carried out under reducing condition, such as, for instance, in the presence of molecular hydrogen and a hydrogenation catalyst in a suitable solvent such as ethanol, methanol, ethyl acetate, or a mixture thereof. The catalyst is usually a metal, most often a palladium derivative such as, for instance, palladium on carbon, palladium hydroxide or palladium black. Preferably, when the protective group is tert-butoxycarbonyl, the reaction may be carried out in the presence of hydrochloric acid, methanesulfonic acid or trifluoroacetic acid in a suitable solvent such as dioxane, dichloromethane, tetrahydrofuran at a temperature ranging from room temperature to reflux and for a time ranging from about 1 hour to about 24 hours. According to the conversion described under 2Cv), the reductive amination of a compound of formula (I), (VIII) or (X) may be carried out in different ways and experimental conditions. Preferably, this reaction is carried out in a suitable solvent such as, for instance, methanol, N,N-dimethylformamide, N,N-dimethylacetamide, dichloromethane, tetrahydrofuran, benzene, toluene, or a mixture thereof, in the presence of a suitable reducing agent such as, for instance, sodium borohydride, tetraalkylammonium borohydride, sodium cyanoborohydride, sodium triacetoxyborohydride, tetramethylammonium triacetoxy borohydride and in presence of an acid or basic catalyst, such as, for instance, acetic acid, trifluoroacetic acid, zinc chloride, zinc bromide, tin(IV) chloride, titanium(IV) chloride, boron trifluoride or triethylamine, N,N-diisopropylethylamine, pyridine at a temperature ranging from about 0° C. to reflux and for a time ranging from about 1 hour to about 96 hours.

According to the conversion described under 3Cv) the derivatization of a compound of formula (I), (VIII), or (X) can be carried out in different ways and experimental conditions. Preferably, this reaction is carried out in a suitable solvent such as, for instance, tetrahydrofuran, dichloromethane, ethyl acetate, diethyl ether, 1,4-dioxane, N,N-dimethylformamide, N,N-dimethylacetamide, dimethoxyethane, in the presence of a suitable base, such as, for instance, sodium or potassium hydride, sodium or potassium hydroxide, sodium, potassium or cesium carbonate, triethylamine, N,N-diisopropylethylamine and the like, at a temperature ranging from room temperature to reflux and for a time ranging from about 10 minutes to about 24 hours. The alkylating agent is usually a halogen or a sulphonate derivative; most often the leaving group is a chloride, bromide, iodide, p-toluenesulfonate, trifluoromethanesulfonate or methanesulfonate anion. Alternatively, the reaction can be carried out under metal-mediated coupling conditions, in the presence of an aromatic or heteroaromatic halogen-derivative such as chloride, bromide, iodide. Preferably, it is carried out in a suitable solvent such as N,N-dimethylformamide, N,N-dimethylacetamide, dimethoxyethane, dioxane, with the use of a catalytic amount of palladium acetate, 2,2'-bis(diphenylphosphino)-1,1'-binaphthyl (BINAP), tris(dibenzylideneacetone)dipalladium (0), 4,5-bis(diphenylphosphino)-9,9-dimethylxanthene (XANTPHOS) and a base such as, for instance, potassium phosphate, potassium or cesium carbonate at a temperature ranging from room temperature to 150° C. and for a time ranging from 2 hours to about 24 hours.

Substituted indazolones can be prepared using standard procedures in organic synthesis as reported, for instance, in Smith, Michael—March's Advanced Organic Chemistry: reactions mechanisms and structure—6th Edition, Michael B. Smith and Jerry March, John Wiley & Sons Inc., New York (N.Y.), 2007. It is known to the skilled person that conversion of a chemical function into another may require that one or more reactive centers in the compound containing this function need to be protected in order to avoid undesired side reactions. Protection of such reactive centers, and subsequent deprotection at the end of the synthetic conversions, can be accomplished following standard procedures described, for instance, in: Greene, Theodora W. and Wuts, Peter G. M.—Protective Groups in Organic Synthesis, Third Edition, John Wiley & Sons Inc., New York (N.Y.), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—Enantiomers, Racemates, and Resolutions, John Wiley & Sons Inc., New York (N.Y.), 1981.

As stated above, a compound of formula (I) can be converted into a pharmaceutically acceptable salt according to standard procedures that are known to those skilled in the art. Alternatively, a compound of formula (I) that is obtained as a salt can be converted into the corresponding free base or the free acid according to standard procedures that are known to the skilled person.

The starting materials of the process of the present invention, i.e. compounds of formula (VII), are either commercially available or can be prepared by using well-known methods. Compounds of general formula (IX) are either commercially available or can be prepared by using well-known methods, for example through alkylation (see, for example, Bioorg. Med. Chem. Lett 2007, 17, 6572-6575) or reductive amination (see, for example, J. Med. Chem. 2010, 53, 3517-3531) of protected hydrazines with the suitable $R_1$ source or by protection of the already substituted (unprotected) hydrazine (see, for example, Bioorg. Med. Chem. Lett. 2005, 15, 5499-5503).

Pharmacology

PARP-1 is a DNA damage-induced polymerase that catalyzes the cleavage of NAD+ into nicotinamide and ADP-ribose and then uses the latter to synthesize branched nucleic-acid like poly(ADP-ribose) polymers. In vivo, the most abundantly poly (ADP-ribosylated) protein is PARP-1 itself, followed by histones. PARP-1 is responsible for 90% of this DNA damage-induced activity while the remaining 10% is due to PARP-2.

Biochemical Assay

Affinity evaluation of the tested compounds and their selectivity with respect to the different PARP isoforms of interest was assessed in a displacement assay.

The identification of compounds capable of binding several PARP proteins is carried out through a screening method including the steps of
a) providing a reaction mixture containing:
the PARP protein isoform under investigation,
a compound of formula (IP):

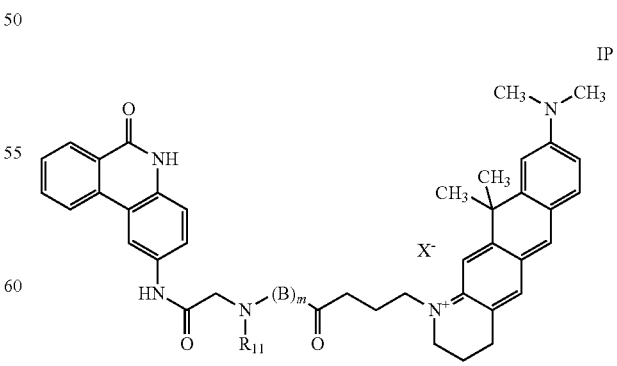

wherein $R_{11}$ is hydrogen or a methyl group, B is $(CH_2)_n$—NH group wherein n is 2 to 6; m is 0 or 1 and $X^-$ is a counterion, and serial dilutions of the test compound;

b) comparing the polarization signal generated in the absence of the test compound with the one generated in the presence of different concentrations of the test compound, and c) evaluating the ability of the test compound to displace the compound of formula (IP) as defined above indicated from a decreased fluorescence polarization level.

Preferably, for the screening method above cited, both the PARP protein and the 5H-phenanthridin-6-one-derived probe of formula (IP) are pre-mixed, or the PARP protein and the test compound are pre-mixed. In a further preferred screening method, the PARP proteins are PARP-1, PARP-2 and PARP-3. The term "PARP protein" encompasses full-length native proteins as well as fragment thereof. More preferably, $R_{11}$ is hydrogen or methyl, m is 0 or 1; when m is 1, n is 3 or 6, $X^-$ is trifluoroacetate. The 5H-phenanthridin-6-one-derived probe (IP) was selected for its capability of binding to the PARP proteins, both encompassing full-length native proteins and fragment thereof.

P3. 9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2,3-g]quinolinium trifluoroacetate.

A compound of formula (IP) as defined above can be prepared as described in WO 2010/133647.

The assay is based on the use of a probe of formula (IP) that binds to the NAD binding pocket and takes advantage of the significant change in the polarization signal observed upon binding of the probe to PARP-1, -2 and -3. The ability of the probe of formula (IP) to bind full-length PARP-1, -2 and -3 has been previously reported (WO 2010/133647). The assay has been validated as described in WO 2010/133647.

Affinity binding constants (Kd) and DC50s (the compound concentration at which the polarization signal is diminished by 50% compared to untreated controls) of the test compounds can be determined as explained in WO 2010/133647.

The assay, by using either probe P1 or probe P3, was used to evaluate the biochemical potency of compounds of formula (I), as reported in Table 1.

TABLE 1

| Compound | PARP-1 ($DC_{50}$ μM) | PARP-1 (Kd μM)* | PARP-2 ($DC_{50}$ μM) | PARP-2 (Kd μM) | PARP-3 ($DC_{50}$ μM) | PARP-3 (Kd μM) |
|---|---|---|---|---|---|---|
| (1) | <0.25† | 0.08 | 1.5 | 0.78 | 0.58 | — |
| (2) | <0.25 | 0.05 | 2 | 1.49 | >10 | — |
| (3) | <0.25 | 0.06 | >10 | — | >10 | — |
| (4) | <0.25 | 0.06 | >10 | — | >10 | — |
| (5) | <0.25 | <0.01† | 0.91 | 0.54 | 2.15 | — |
| (6) | <0.25 | <0.01 | 3.95 | 1.88 | 2.34 | — |
| (7) | <0.25 | <0.01 | <0.25 | 0.05 | 2.58 | — |
| (8) | <0.25 | 0.14 | <0.25 | 0.04 | 2.75 | — |
| (9) | <0.25 | 0.014 | <0.25 | 0.14 | 0.45 | — |
| (14) | <0.25 | 0.011 | <0.25 | 0.03 | >10 | — |
| (16) | 0.49 | 0.22 | 2.57 | — | >10 | — |
| (18) | <0.25 | <0.01 | <0.25 | — | 2.88 | — |
| (20) | <0.25 | <0.01 | 0.5 | 0.3 | 0.25 | 0.05 |
| (21) | <0.25 | <0.01 | <0.25 | 0.07 | 0.22 | 0.04 |
| (22) | <0.25 | <0.01 | 0.79 | 0.5 | 0.7 | 0.27 |
| (23) | <0.25 | 0.03 | 5.94 | 5 | >10 | — |
| (31) | 0.26 | 0.06 | >10 | — | >10 | — |
| (33) | <0.25 | 0.022 | >10 | — | 2.9 | — |
| (62) | <0.25 | 0.022 | >10 | — | 0.46 | — |
| (65) | <0.25 | 0.011 | 4.19 | — | 1.78 | — |
| (64) | <0.25 | 0.12 | >10 | — | >10 | — |
| (66) | <0.25 | 0.14 | >10 | — | 0.58 | — |
| (63) | <0.25 | <0.01 | 3.56 | — | 1.42 | — |
| (67) | <0.25 | 0.015 | 2.29 | — | 2.56 | — |

*Assay performed with compound P3 as the probe. In all other cases compound P1 was used as the probe.
†Assay sensitivity limits based on a fitting error <50%.

The polarization signal can be measured, e.g., by a plate reader such as the Saphire2 (Tecan). Data analysis was performed, e.g., by using the Dynafit software. Displacement data were also fitted, e.g., by using Excel spreadsheet (Microsoft Inc. Seattle, USA) to a four parameter logistic model (4PL), or Hill-Slope model. The assay was used to test compounds of the present invention. The displacement ability of the test compounds of formula (I) is in correlation with the compounds affinity for the NAD pocket of the enzyme. Specific probes of formula (IP) used in the assay are:

P1. 9-Dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate;

P2. 9-Dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho[2,3-g]quinolinium trifluoroacetate;

From the above data, it is clear to a person skilled in the art that compounds of formula (I) of the present invention are highly potent as PARP-1 inhibitors and extremely selective versus PARP-2 and PARP-3 (compare PARP-1, PARP-2 and PARP-3 $DC_{50}$ and Kd values in Table 1 above).

Cellular Assay

PAR Assay

Cellular activity of PARP-1 inhibitors was assessed by measuring the inhibition of the hydrogen peroxide induced PAR formation in HeLa cells (ECACC). Cellular PAR levels were measured by immunocytochemistry, and quantified using an ArrayScan vTi instrument (Cellomics Thermo Scientific).

Studies were performed as follows: 6000 cells/well were seeded in 96 well plates (Perkin Elmer) in MEM/10% FCS and incubated for 24 hours at 37° C., 5% carbon dioxide. Test compounds were then added at the required concentration for 30 minutes. DNA damage was then induced adding hydrogen peroxide at the concentration of 0.1 mM for 15 minutes.

Concentration curves were prepared in MEM/10% FCS from compound stocks in DMSO, and final DMSO concentration was 0.002% (v/v). Duplicate wells for each concentration point were prepared with a typical highest compound concentration of 20 µM and serial dilution 1:3. Plates were dried and fixed adding cold methanol-acetone (70:30) solution for 15 minutes at room temperature, fixing solution was aspired and wells were air dried for 5 minutes and then dehydrated in PBS. Non-specific binding sites were blocked by incubating wells for 30 minutes in PBS containing 5% (w/v) FBS 0.05% tween20. Wells were then incubated for 1 hour at room temperature in PBS containing anti PAR mouse monoclonal antibody (Anti-PAR, Mouse mAb 10H, Tulip Cat N° 1020) diluted 1:200 in blocking solution. After 3 washes in PBS, wells incubated in PBS (w/v) 5% FBS 0.05% Tween20 containing 2 µg/mL Cy2-conjugated Goat anti mouse secondary antibody (Amersham Pharmacia Biotech cat. N° PA 42002) (Absorption maximum 489 nm fluorescence maximum 506 nm) and 1 µg/mL DAPI (Absorption maximum 359 nm fluorescence maximum 461 nm) (4',6-diamidino-2-phenylindole dilactate) (Sigma cat. N° D9564), a high sensitivity dye for nucleic acid staining. After washing further 3 times in PBS, cellular PAR immunoreactivity was assessed using the Array-Scan vTi instrument, with a Zeiss 10×0.5 N.A. objective, and applying the Cytotoxicity. V3 algorithm (Cellomics/Thermo Fisher) with a XF100 filter. At least 10 fields, corresponding to at least 900 cells, were read for each well. $IC_{50}$ Values represent the compound concentration at which cellular PAR signal is diminished by 50% compared with untreated controls.

The following formula is used:

$$IC_{50}=Bottom+(Top-Bottom)/(1+10^{\wedge}((Log\ EC_{50}-X)));$$

X is the logarithm of concentration, $IC_{50}$ is the response; $IC_{50}$ starts at bottom and goes to top with a sigmoid shape. Given the above assays, compounds of formula (I) of the present invention inhibited PAR formation with $IC_{50}$ values lower than 1 µM, as depicted in Table 2.

TABLE 2

| Compound | PAR assay ($IC_{50}$ µM) | Compound | PAR assay ($IC_{50}$ µM) |
|---|---|---|---|
| (2) | 0.24 | (22) | 0.015 |
| (3) | 0.23 | (23) | 0.34 |
| (4) | 0.15 | (31) | 0.095 |
| (5) | 0.026 | (33) | 0.19 |
| (6) | 0.10 | (62) | 0.07 |
| (7) | 0.13 | (63) | 0.13 |
| (8) | 0.6 | (64) | 0.15 |
| (9) | 0.05 | (65) | 0.044 |
| (14) | 0.13 | (66) | 0.23 |
| (16) | 2.5 | (67) | 1.3 |
| (18) | 0.023 | | |

Colony Forming Assay

MDA-MB-436 breast cancer BRCA-1 mutated cells were grown at the density of 600 cells/cm² in RPMI medium supplemented with 10% Fetal Bovine Serum. 24 Hours later different doses of compounds were added starting from 10 µM concentration in duplicates. Ten days later, cells were fixed and stained with crystal violet. Colonies were counted using Infrared Scanner (Odyssey Li-Cor). Anti proliferative $IC_{50}$ was calculated using Prism.

Pharmacokinetics

The pharmacokinetic profile and the oral bioavailability of the compounds have been investigated in the mouse (Balb, Nu/Nu, Harlan, Italy) in ad hoc pharmacokinetic studies. The compounds were formulated in 10% tween 80/dextrose for intravenous bolus administration while oral administrations were performed using the compounds formulated in 0.5% methylcellulose. A single administration at the dose of 10 mg/kg was given and three male animals for each route were used. All blood samples were taken from retro-orbital vein at 5 minutes, 30 minutes, 1 hour, 3 hours, 6 hours, 24 hours after intravenous administration and 15 minutes, 30 minutes, 1 hour, 3 hours, 6 hours, 24 hours after oral administration. Plasma samples were prepared by plasma proteins precipitation adding 200 µL of acetonitrile to 20 µL of plasma in a 96 well plate. After capping and vortex mixing, the plate was centrifuged for 15 minutes at 4000 rpm. The supernatant was considered as final extract and injected onto the LC-MS-MS system (UPLC system: Waters Acquity using BEH C18 50*2.1 mm 1.7 µm analytical column; MS instrument: Waters TQD equipped with Electro-Spray source operating in positive ion mode). Lower limit of quantification is 5.0 ng/mL, upper limit of quantification is 5000 ng/mL. Non-compartmental method (linear trapezoidal rule and linear regression analysis of natural log-transformed plasma concentrations vs. time data) was used. Absolute bioavailability (F) was calculated from the ratio of average oral to IV (intravenous) dose-normalized plasma AUC (area under curve) values.

The abbreviations used herein have the following meaning:

AUC (area under the plasma concentration vs. time curve up to the last detectable concentration)

Cl (plasma clearance)

Cmax (maximum plasma concentration)

T½ (terminal half life)

Vdss (volume of distribution at steady state)

Some representative compounds of formula (I) were evaluated for their pharmacokinetic parameters as reported in Table 3 as mean value.

TABLE 3

| Compound | CL (IV bolus) ml/min/kg | Vdss (IV bolus) L/Kg | AUC (oral) µM · hours | C-max (oral) µM | T½ (oral) hours | F on AUC % |
|---|---|---|---|---|---|---|
| (3) | 17.8 | 1.3 | 14.35 | 5.6 | 1.77 | 67 |
| (5) | 41 | 4.3 | 10.58 | 4.77 | 1.89 | 109 |
| (6) | 52.7 | 2.9 | 3.87 | 3.07 | 1.13 | 49 |
| (22) | 38.7 | 6.4 | 12.76 | 4.72 | 2.25 | 150 |
| (65) | 53.8 | 3.4 | 4.06 | 1.93 | 1.16 | 50 |

From the above, it is clear to the person skilled in the art that compounds of formula (I) possess good to excellent pharmacokinetics profiles and oral bioavailability.

In Vivo Efficacy Studies

CD1, athymic Nu/Nu male mice, from Charles River (Italy), were maintained—in agreement with the European Communities Council Directive no. 86/609/EEC, concerning the protection of animals used for experimental or other scientific purposes—in cages with paper filter cover, food and bedding sterilized and acidified water. Fragments of Capan-1 human pancreatic cancer tumors were implanted subcutaneously. Mice bearing a palpable tumor (100-200 mm³) were selected and randomized into control and treated groups. Each group included seven animals. The treatment started one day after randomization. Compounds of formula (I) were administered by oral route as a methocel suspension. Tumor dimension was measured regularly by calipers during the experiments and tumor mass was calculated as described in Simeoni M. et al., Cancer Res 2004, 64, 1094-1101. The tumor growth inhibition (TGI, %) was calculated according to the equation: % TGI=100-(mean tumor weight of treated group/mean tumor weight of control group)*100.

A representative compound of formula (I), cpd 3, was evaluated for its anti-tumor activity on Capan-1 BRCA-2 mutated mouse model in combination with temozolomide. Cpd 3 was administered by oral route at the dose of 200 mg/kg daily for twelve consecutive days (days 1 to 12). Temozolomide was administered by oral route at the dose of 50 mg/kg on days 3, 4, 5, 6, 7 and 8. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor compared to temozolomide alone (see for references Anticancer drugs 1996, 7, 437-460). This delay (T–C value) was defined as the difference of time (in days) required for the treatment group (T) and the control group (C) tumors to reach a predetermined size (1 g). Toxicity was evaluated on the basis of body weight reduction and animal survival rate. The results are reported in Table 4.

TABLE 4

| Treatment | Max TGI (%) | BWL (%) | T-C (days) | Toxicity |
|---|---|---|---|---|
| temozolomide 50 mg/kg* | 13 | 2 | 1 | 0/7 |
| temozolomide 50 mg/kg + cpd 3 200 mg/kg** | 79 | 8 | 24 | 0/7 |

*Treatments made by oral route once a day at days 3, 4, 5, 6, 7 and 8.
**Cpd. 3 treatments by oral route on day 1 to 12 daily, temozolomide treatments once a day at days 3, 4, 5, 6, 7 and 8.

The T–C delay observed when cpd. 3 was combined with temozolomide proved to be superior to the corresponding delay observed with temozolomide alone.

From the above, it is clear to the person skilled in the art that compounds of formula (I) possess good tumor growth inhibition activities in combination with cytotoxic agents.

Therefore, the present invention provides compounds of formula (I) useful in therapy.

Compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 1 to about 1000 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

As stated above, the present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
μM (micromolar)
μL (microliter)
μm (micrometer)
mol (moles)
mM (millimolar)
mmol (millimoles)
nm (nanometers)
g (grams)
mg (milligrams)
$DC_{50}$ (the half maximal Displacement Concentration)
$IC_{50}$ (the half maximal Inhibitory Concentration)
PAR (poly (ADP-ribose)
MEM (Minimal Essential Medium)
FCS (Fetal Calf Serum)
FBS (Fetal Bovine Serum)
PBS (Phosphate Buffered Saline)
LC-MS (Liquid Chromatography-Mass Spectrometry)
HPLC (High Performance Liquid Chromatography)
TLC (Thin Layer Chromatography)
MHz (megahertz)
Hz (Hertz)
DMSO (dimethylsulfoxide)
ESI (electrospray ionization)
With the aim at better illustrating the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as N,N-dimethylformamide, tetrahydrofuran, dichloromethane and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60 Å). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and mobile phase B was water-acetonitrile (5:95). Gradient from 10 to 90% B in 8 minutes, hold 90% B 2 minutes. UV detection at 220 nm and 254 nm. Flow rate 1 mL/minute. Injection volume 10 μL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 μm) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 minutes, hold 90% B 2 minutes. Flow rate 20 mL/minute. In alternative, mobile phase A was water-0.1% ammonium hydroxide, and mobile phase B was acetonitrile. Gradient from 10 to 100% B in 8 minutes, hold 100% B 2 minutes. Flow rate 20 mL/minute.

$^1$H-NMR spectra were performed in DMSO-d$_6$ on a Varian Inova 400, 500 and 600 operating respectively at 400.5, 499.8 and 599.9 MHz.

Example 1

Step a

2-Bromo-6-iodobenzoic acid (VI)

Hal$_1$=Br; Hal$_2$=I; R$_3$=H 2-bromobenzoic acid (20.1 g, 100 mmol), palladium(II) acetate (1.12 mg, 5 mmol), iodobenzene diacetate (38.64 g, 120 mmol) and elemental iodine (30.48 g, 120 mmol) were dissolved in N,N-dimethylformamide (240 mL) and stirred overnight at 100° C. The reaction mixture was cooled to room temperature, diluted with methyl-tert-butylether and 2M hydrochloric acid and washed with 10% aqueous solution of sodium metabisulphite. Organic phase was extracted with 2M sodium hydroxide and the resulting basic aqueous phase was acidified with concentrated aqueous hydrochloric acid and re-extracted with methyl-tert-butylether. The solvent was removed under reduced pressure affording 2-bromo-6-iodobenzoic acid (24.3 g, 74% yield), which was used in the next step without further purification.

$^1$H NMR (400.5 MHz, DMSO-d$_6$) δ ppm 7.09 (dd, J=7.8, 7.9 Hz, 1H), 7.68 (d, J=7.9 Hz, 1H), 7.87 (d, J=7.8 Hz, 1H).

Operating in an analogous way, but employing 2-bromo-4-fluorobenzoic acid as starting material, the following compound was obtained:

2-Bromo-4-fluoro-6-iodobenzoic acid (VI)

Hal$_1$=Br; Hal$_2$=I; R$_3$=F $^1$H NMR (599.9 MHz, DMSO-d$_6$) δ ppm 7.73 (dd, J=8.4, 2.4 Hz, 1H) 7.85 (dd, J=8.1, 2.4 Hz, 1H) 13.91 (br. s., 1H).

Preparation of Intermediate of Formula (IX)

4-(N'-ethoxycarbonyl-hydrazino)-piperidine-1-carboxylic acid tert-butyl ester

R$_1$=1-(tert-butoxycarbonyl)piperidin-4-yl; T=ethyl

To a stirred solution of tert-butyl 4-oxopiperidine-1-carboxylate (1 g, 5 mmol) and ethyl hydrazinecarboxylate (650 mg, 6.22 mmol) in MeOH (17.5 mL) acetic acid (0.28 mL) was added. The reaction was poured in an ice bath and NaCNBH$_3$ (630 mg, 10 mmol) was added. Then the solution was allowed to reach room temperature and was stirred for 9 hours, until a TLC control revealed the disappearance of the tert-butyl 4-oxopiperidine-1-carboxylate. The solvent was removed under reduce pressure and the residue was dissolved in ethyl acetate. NaOH 5N (2 mL) was added and the mixture was stirred for 10 minutes. Then the solution was washed twice with water and the organic phase was dried over anhydrous sodium sulphate and concentrated in vacuo. The crude was purified by flash chromatography (hexane/ethyl acetate 6:4) to obtain the title compound (1.12 g, 78%) as a yellow oil.

$^1$H NMR (400.5 MHz, DMSO-d$_6$) δ ppm 1.07-1.14 (m, 2H), 1.15 (t, J=7.1 Hz, 3H), 1.38 (s, 9H), 1.57-1.69 (m, 2H), 2.80-2.93 (m, 3H), 3.68-3.77 (m, 2H), 4.00 (q, J=7.1 Hz, 2H), 4.45-4.47 (m, 1H), 8.41 (br. s., 1H).

Step b

Tert-butyl 4-[1-(2-bromo-6-iodobenzoyl)-2-(ethoxycarbonyl)hydrazinyl]piperidine-1-carboxylate (V)

Hal$_1$=Br; Hal$_2$=I; R$_1$=1-(tert-butoxycarbonyl)piperidin-4-yl; R$_3$=H; T=ethyl To a stirred solution of 2-bromo-6-iodobenzoic acid (12 g, 36.6 mmol) and oxalyl chloride (6.2 mL, 73.3 mmol) in dichloromethane (570 mL), a catalytic amount of N,N-dimethylformamide (20 μL) was added. The reaction was stirred under N$_2$ atmosphere for 1 hour. The solvent was removed under reduce pressure and the residue was dissolved with dichloromethane (240 mL). 4-(N'-Ethoxycarbonyl-hydrazino)-piperidine-1-carboxylic acid tert-butyl ester (IX) (11.5 g, 40.2 mmol) and N,N-diisopropylethylamine (25.5 mL, 146.4 mmol) were added, and the mixture was stirred at room temperature for 18 hours. Volatiles were removed under reduce pressure and the crude was diluted with dichloromethane. The solution was washed twice with water and the organic phase was dried over anhydrous sodium sulphate and concentrated in vacuo. The crude was purified by flash chromatography (cyclohexane/acetone 8:2) to obtained the desired product (14.34 g, 66%).

$^1$H NMR (400.5 MHz, DMSO-d$_6$, temp=70° C., mixture of isomers in a 1.3/1 ratio) δ ppm 1.07 (t, J=7.2 Hz, 3×0.56H), 1.24 (t, J=7.2 Hz, 3×0.43H), 1.38 (s, 9×0.43H), 1.42 (s, 9×0.56H), 1.40-2.00 (m, 4H), 2.50-2.60 (m, 2×0.43H), 2.80-2.90 (m, 2×0.56H), 3.35-3.44 (m, 0.43H), 3.85-4.20 (m, 4H), 4.42-4.53 (m, 0.56H), 6.99 (dd, J=7.9, 8.1 Hz, 0.56H), 7.11 (dd, J=7.9, 8.1 Hz, 0.43H), 7.60 (d, J=8.1 Hz, 0.56H), 7.72 (d, J=8.1 Hz, 0.43H), 7.82 (d, J=7.9 Hz, 0.56H), 7.94 (d, J=7.9 Hz, 0.43H), 8.95 (br. s, 0.56H), 9.15 (br. s, 0.43H).

Operating in an analogous way, but employing 2-bromo-4-fluoro-6-iodobenzoic acid as starting material, the following compound was obtained:

Tert-butyl 4-[1-(2-bromo-4-fluoro-6-iodobenzoyl)-2-(ethoxycarbonyl)hydrazinyl]piperidine-1-carboxylate (V)

$Hal_1$=Br; $Hal_1$=I; $R_1$=1-(tert-butoxycarbonyl)piperidin-4-yl; $R_3$=F; T=ethyl $^1$H NMR (599.9 MHz, DMSO-$d_6$, mixture of isomers in a 1.4/1 ratio) δ ppm 1.01 (br. s., 3×0.6H), 1.25 (br. s., 3×0.4H), 1.37 (s, 9×0.4H), 1.40 (s, 9×0.6H), 1.42-1.93 (br. s., 4H), 2.50-2.90 (br. s., 2H), 3.38-3.48 (br. s., 0.4H), 3.83-4.15 (br. s., 4H), 4.47-4.58 (br. s., 0.6H), 7.60-7.95 (br. s., 2H), 9.0-9.5 (br. s., 1H).

Step c

Ethyl 4-bromo-2-[1-(tert-butoxycarbonyl)piperidin-4-yl]-3-oxo-2,3-dihydro-1H-indazole-1-carboxylate (IV)

$Hal_1$=Br; $R_1$=1-(tert-butoxycarbonyl)piperidin-4-yl; $R_3$=H; T=ethyl

To a degassed solution of cesium carbonate (2.2 g, 6.9 mmol), copper iodide (82 mg, 0.43 mmol) and 1,10-phenanthroline (155 mg, 0.86 mmol) in N,N-dimethylformamide (24 mL), tert-butyl 4-[1-(2-bromo-6-iodobenzoyl)-2-(ethoxycarbonyl)hydrazinyl]piperidine-1-carboxylate (2.6 g, 4.3 mmol) was added. The reaction mixture was heated at 80° C. for 3 hours and then diluted with ethyl acetate. The resulting solution was washed with 10% ammonium hydroxide, water and 10% copper sulphate. Organic layers were collected, dried over sodium sulphate and evaporated. The crude was purified by flash chromatography (hexane/ethyl acetate 7:3) to give the desired product (8.2 g, 70%).

$^1$H NMR (400.5 MHz, DMSO-$d_6$) δ ppm 1.36 (t, J=7.1 Hz, 3H), 1.42 (s, 9H), 1.79 (d, J=10.4 Hz, 2H), 2.12-2.23 (m, 2H), 2.75 (br. s., 2H), 4.06 (br. s., 2H), 4.16-4.29 (m, 1H), 4.39 (d, J=7.1 Hz, 2H), 7.56 (dd, J=7.8, 0.8 Hz, 1H), 7.61 (dd, J=8.1, 7.8 Hz, 1H), 7.85 (dd, J=8.1, 0.8 Hz, 1H).

Operating in an analogous way, but employing tert-butyl 4-[1-(2-bromo-4-fluoro-6-iodobenzoyl)-2-(ethoxycarbonyl)hydrazinyl]piperidine-1-carboxylate as starting material, the following compound was obtained:

Ethyl 4-bromo-2-[1-(tert-butoxycarbonyl)piperidin-4-yl]-6-fluoro-3-oxo-2,3-dihydro-1H-indazole-1-carboxylate (IV)

$Hal_1$=Br; $R_1$=1-(tert-butoxycarbonyl)piperidin-4-yl; $R_3$=F; T=ethyl $^1$H NMR (599.9 MHz, DMSO-$d_6$) δ ppm 1.36 (t, J=7.1 Hz, 3H) 1.41 (s, 9H) 1.79 (d, J=13.0 Hz, 2H) 2.10-2.20 (m, 2H) 2.75 (br. s., 2H) 4.05 (br. s., 2H) 4.19-4.24 (m, 1H) 4.39 (q, J=7.1 Hz, 2H) 7.59 (dd, $J_{HF}$=8.8, $J_{HH}$=2.0 Hz, 1H) 7.62 (dd, $J_{HF}$=9.5, $J_{HH}$=2.0 Hz, 1H).

Step d

Ethyl 2-[1-(tert-butoxycarbonyl)piperidin-4-yl]-4-cyano-3-oxo-2,3-dihydro-1H-indazole-1-carboxylate (III)

$R_1$=1-(tert-butoxycarbonyl)piperidin-4-yl; $R_3$=H; T=ethyl

To a degassed solution of tris(dibenzylideneacetone)dipalladium(0) (78 mg, 0.08 mmol), tri-tert-butylphosphonium tetrafluoroborate (79 mg, 0.27 mmol), zinc cyanide (435 mg, 3.7 mmol) and zinc powder (59 mg, 0.9 mmol) in N-methyl-2-pyrrolidone (70 mL), ethyl 4-bromo-2-[1-(tert-butoxycarbonyl)piperidin-4-yl]-3-oxo-2,3-dihydro-1H-indazole-1-carboxylate (800 mg, 1.7 mmol) was added. The reaction mixture was heated at 80° C. for 3 hours and then cooled to room temperature and diluted with ethyl acetate. Zn powder was filtered-off and the resulting solution was washed with water and brine. Organic layers were collected, dried over sodium sulphate and evaporated. The crude was purified by flash chromatography (hexane/ethyl acetate 6:4) to obtain the desired product (597 mg, 85%).

$^1$H NMR (400.5 MHz, DMSO-$d_6$) δ ppm 1.38 (t, J=7.1 Hz, 3H), 1.42 (s, 9H), 1.82 (d, J=13.0 Hz, 2H), 2.15-2.26 (m, 2H), 2.75 (br. s., 2H), 4.06 (br. s, 2H), 4.25-4.35 (m, 1H), 4.40 (q, J=7.1 Hz, 2H), 7.86-7.92 (m, 2H), 8.12-8.18 (m, 1H).

Ethyl 2-[1-(tert-butoxycarbonyl)piperidin-4-yl]-4-cyano-6-fluoro-3-oxo-2,3-dihydro-1H-indazole-1-carboxylate (III)

$R_1$=1-(tert-butoxycarbonyl)piperidin-4-yl; $R_3$=F; T=ethyl

To a degassed solution of tris(dibenzylideneacetone)dipalladium(0) (188 mg, 0.2 mmol), 1,1'-bis(diphenylphosphino)ferrocene (228 mg, 0.41 mmol) and zinc cyanide (483 mg, 4.11 mmol) in N,N-dimethylformamide (20 mL), ethyl 4-bromo-2-[1-(tert-butoxycarbonyl)piperidin-4-yl]-6-fluoro-3-oxo-2,3-dihydro-1H-indazole-1-carboxylate (2 g, 4.11 mmol) was added. The reaction mixture was heated at 95° C. for 2 hours and then cooled to room temperature, diluted with ethyl acetate, washed with 10% aqueous ammonia, water and brine. The organic layer was finally dried over sodium sulphate and evaporated to dryness. The resulting crude was purified by flash chromatography (hexane/ethyl acetate 6:4) to obtain the desired product (1.31 g, 74%).

$^1$H NMR (599.9 MHz, DMSO-$d_6$) δ ppm 1.37 (t, J=7.1 Hz, 3H) 1.42 (s, 9H) 1.82 (d, J=12.0 Hz, 2H) 2.13-2.22 (m, 2H) 2.75 (br. s., 2H) 4.06 (br. s., 2H) 4.25-4.33 (m, 1H) 4.41 (q, J=7.1 Hz, 2H) 7.93 (dd, $J_{HF}$=9.2, $J_{HH}$=2.2 Hz, 1H) 7.97 (dd, $J_{HF}$=9.0, $J_{HH}$=2.2 Hz, 1H).

Step e

Ethyl 2-[1-(tert-butoxycarbonyl)piperidin-4-yl]-4-carbamoyl-3-oxo-2,3-dihydro-1H-indazole-1-carboxylate (I)

$R_1$=1-(tert-butoxycarbonyl)piperidin-4-yl; $R_2$=ethoxycarbonyl; $R_3$=H

To a solution of ethyl 2-[1-(tert-butoxycarbonyl)piperidin-4-yl]-4-cyano-3-oxo-2,3-dihydro-1H-indazole-1-carboxylate (630 mg, 1.5 mmol) in toluene (36 mL), acetaldoxime (0.940 mL, 1.5 mmol) and indium(III) chloride (16.5 mg, 0.07 mmol) were added at room temperature. The resulting solution was heated at 120° C. for 3 hours until the disappearance of the starting material, as judged by HPLC. Volatiles were removed under reduced pressure to afford the desired product (640 mg, 97% yield) as a yellow solid.

$^1$H NMR (499.8 MHz, DMSO-d$_6$) δ ppm 1.37 (t, J=7.1 Hz, 3H), 1.42 (s, 9H), 1.83 (d, J=11.8 Hz, 2H), 2.17-2.29 (m, 2H), 2.76 (br. s., 2H), 4.06 (br. s., 2H), 4.30-4.36 (m, 1H), 4.41 (q, J=7.1 Hz, 2H), 7.82 (br. s., 1H), 7.84 (dd, J=8.5, 7.7 Hz, 1H), 7.99 (dd, J=7.7, 1.1 Hz, 1H), 8.07 (dd, J=8.5, 1.1 Hz, 1H), 9.87 (br. s., 1H).

Operating in an analogous way, but employing ethyl 2-[1-(tert-butoxycarbonyl)piperidin-4-yl]-4-cyano-6-fluoro-3-oxo-2,3-dihydro-1H-indazole-1-carboxylate as starting material, the following compound was obtained:

Ethyl 2-[1-(tert-butoxycarbonyl)piperidin-4-yl]-4-carbamoyl-6-fluoro-3-oxo-2,3-dihydro-1H-indazole-1-carboxylate (I)

$R_1$=1-(tert-butoxycarbonyl)piperidin-4-yl; $R_2$=ethoxycarbonyl; $R_3$=F

MS m/z=451 (MH$^+$).

Step f

Tert-butyl 4-(4-carbamoyl-3-oxo-1,3-dihydro-2H-indazol-2-yl)piperidine-1-carboxylate (I)

$R_1$=1-(tert-butoxycarbonyl)piperidin-4-yl; $R_2$=$R_3$=H

A solution of ethyl 2-[1-(tert-butoxycarbonyl)piperidin-4-yl]-4-carbamoyl-3-oxo-2,3-dihydro-1H-indazole-1-carboxylate (70 mg, 0.16 mmol) and triethylamine (0.17 mL, 1.2 mmol) in methanol (1.7 mL) was heated at 80° C. for 3 hours.

The solvent was removed under reduced pressure and the crude was purified by flash chromatography (dichloromethane/methanol 95:5) to obtain the desired product (65 mg, 90% over two steps).

$^1$H NMR (599.9 MHz, DMSO-d$_6$) δ ppm 1.43 (s, 9H), 1.78-1.86 (m, 4H), 2.91 (br. s., 2H), 4.09 (br. s., 2H), 4.53-4.59 (m, 1H), 7.45 (d, J=8.2 Hz, 1H), 7.60 (br. s., 1H), 7.61 (dd, J=8.2, 7.3 Hz, 1H), 7.85 (d, J=7.3 Hz, 1H), 10.96 (br. s., 1H), 11.01 (br. s., 1H).

Operating in an analogous way, but employing ethyl 2-[1-(tert-butoxycarbonyl)piperidin-4-yl]-4-cyano-6-fluoro-3-oxo-2,3-dihydro-1H-indazole-1-carboxylate as starting material the following compound was obtained:

Tert-butyl 4-(4-carbamoyl-6-fluoro-3-oxo-1,3-dihydro-2H-indazol-2-yl)piperidine-1-carboxylate (I)

$R_1$=1-(tert-butoxycarbonyl)piperidin-4-yl; $R_2$=H; $R_3$=F $^1$H NMR (599.9 MHz, DMSO-d$_6$) δ ppm 1.43 (s, 9H) 1.77-1.87 (m, 4H) 2.92 (br. s., 2H) 4.08 (br. s., 2H) 4.52-4.57 (m, 1H) 7.29 (dd, $J_{HF}$=8.4, $J_{HH}$=2.0 Hz, 2H) 7.54 (dd, $J_{HF}$=10.8, $J_{HH}$=2.0 Hz, 1H) 7.80 (br. s., 1H) 11.03 (br. s., 1H) 11.29 (br. s., 1H).

Conversion 1

3-Oxo-2-(piperidin-4-yl)-2,3-dihydro-1H-indazole-4-carboxamide (I), cpd 1

$R_1$=piperidin-4-yl; $R_2$=$R_3$=H

A solution of ethyl tert-butyl 4-(4-carbamoyl-3-oxo-1,3-dihydro-2H-indazol-2-yl)piperidine-1-carboxylate (620 mg, 1.7 mmol) in 4M hydrochloric acid in dioxane (4.3 mL, 1.7 mmol) was stirred at 50° C. for 3 hours until HPLC analysis revealed the disappearance of the starting material. The solvent was removed under reduced pressure and the product was dissolved in diethyl ether and filtered to obtain the title compound (500 mg, 95%) as its hydrochloride.

$^1$H NMR (599.9 MHz, DMSO-d$_6$) δ ppm 2.01 (d, J=13.0 Hz, 2H), 2.12-2.21 (m, 2H), 3.08-3.18 (m, 2H), 3.40 (signal overlapped by water, 2H), 4.63-4.69 (m, 1H), 7.51 (d, J=8.2 Hz, 1H) 7.63 (dd, J=8.2, 7.5 Hz, 1H), 7.69 (br. s., 1H), 7.86 (d, J=7.5 Hz, 1H), 8.65 (br. s., 1H), 8.89 (br. s., 1H), 10.80 (br. s., 2H).

Operating in an analogous way, but employing tert-butyl 4-(4-carbamoyl-6-fluoro-3-oxo-1,3-dihydro-2H-indazol-2-yl)piperidine-1-carboxylate as starting material, the following compound was obtained:

6-Fluoro-3-oxo-2-(piperidin-4-yl)-2,3-dihydro-1H-indazole-4-carboxamide (I), cpd 20

$R_1$=piperidin-4-yl; $R_2$=H; $R_3$=F $^1$H NMR (599.9 MHz, DMSO-d$_6$) δ ppm 2.00 (d, J=12.8 Hz, 1H) 2.11-2.20 (m, 2H) 3.08-3.18 (m, 2H) 3.40 (signal overlapped by water, 2H) 4.61-4.67 (m, 1H) 7.35 (dd, $J_{HF}$=8.6, $J_{HH}$=2.4 Hz, 1H) 7.58 (dd, $J_{HF}$=10.8, $J_{HH}$=2.4 Hz, 1H) 7.89 (br. s., 1H) 8.67 (br. s., 1H) 8.89 (br. s., 1H) 10.82 (br. s., 1H) 11.28 (br. s., 1H).

Operating in an analogous way, but employing tert-butyl 4-(4-carbamoyl-6-fluoro-1-methyl-3-oxo-1,3-dihydro-2H-indazol-2-yl)piperidine-1-carboxylate as starting material, the following compound was obtained:

6-Fluoro-1-methyl-3-oxo-2-(piperidin-4-yl)-2,3-dihydro-1H-indazole-4-carboxamide (I), cpd 21

$R_1$=piperidin-4-yl; $R_2$=methyl; $R_3$=H $^1$H NMR (599.9 MHz, DMSO-d$_6$) δ ppm 1.92 (d, J=12.6 Hz, 2H) 2.54-2.62 (m, 2H) 2.98-3.06 (m, 2H) 3.39 (signal overlapped by water, 2H) 3.44 (s, 3H) 4.46-4.53 (m, 1H) 7.59 (dd, $J_{HF}$=10.6, $J_{HH}$=2.2 Hz, 1H) 7.73 (dd, $J_{HF}$=9.2, $J_{HH}$=2.2 Hz, 1H) 7.86 (br. s., 1H) 8.64 (br. s., 1H) 8.84 (br. s., 1H) 10.66 (br. s., 1H).

Conversion 2

2-[1-(4,4-Difluorocyclohexyl)piperidin-4-yl]-3-oxo-2,3-dihydro-1H-indazole-4-carboxamide (I), cpd 4

$R_1$=1-(4,4-difluorocyclohexyl)piperidin-4-yl; $R_2$=$R_3$=H

To a suspension of 3-oxo-2-(piperidin-4-yl)-2,3-dihydro-1H-indazole-4-carboxamide hydrochloride (200 mg, 0.67 mmol) in methanol (6 mL) 4,4-difluorocyclohexanone (135 mg, 1 mmol) and sodium acetate (165 mg, 2 mmol) were added. The resulting yellow solution was stirred at room temperature for 15 minutes, then NaCNBH$_3$ 95% (126 mg, 2 mmol) was added and the mixture was stirred at 80° C. for 6 hours. The solvent was removed under reduced pressure and the residue was dissolved in dichloromethane and washed with aqueous sodium hydrogen carbonate saturated solution. The aqueous layer was acidified to pH=5 with acetic acid and extracted with dichloromethane. Organic layers were collected, dried over anhydrous sodium sulfate and concentrated in vacuo. The resulting crude was purified by flash chromatography (dichloromethane/methanol 9:1) to give the title compound (187 mg, 73%).

$^1$H NMR (599.9 MHz, DMSO-$d_6$) δ ppm 1.51-1.61 (m, 2H) 1.74-2.11 (m, 10H), 2.27-2.37 (m, 2H), 2.53 (signal overlapped by DMSO, 1H), 2.95-3.03 (m, 2H), 4.28-4.35 (m, 1H), 7.44 (d, J=8.2 Hz, 1H), 7.58 (br. s., 1H), 7.60 (br. s., 1H), 7.83 (d, J=7.0 Hz, 1H), 10.98 (br. s., 1H), 11.06 (br. s., 1H).

Operating in an analogous way, but employing suitable substituted starting material, the following compounds were obtained:

2-(1-Cyclopentylpiperidin-4-yl)-3-oxo-2,3-dihydro-1H-indazole-4-carboxamide (I), cpd 2

$R_1$=1-cyclopentylpiperidin-4-yl; $R_2$=$R_3$=H $^1$H NMR (599.9 MHz, DMSO-$d_6$) δ ppm 1.36-2.26 (m, 15H), 3.18 (br. s., 2H), 4.39 (br. s., 1H), 7.44 (d, J=8.1 Hz, 1H), 7.57 (br. s., 2H), 7.80 (br. s., 1H), 10.84 (br. s., 1H) 11.06 (br. s., 1H).

2-(1-Cyclohexylpiperidin-4-yl)-3-oxo-2,3-dihydro-1H-indazole-4-carboxamide (I), cpd 3

$R_1$=1-cyclohexylpiperidin-4-yl; $R_2$=$R_3$=H $^1$H NMR (599.9 MHz, DMSO-$d_6$) δ ppm 1.05-1.13 (m, 1H), 1.19-1.32 (m, 4H), 1.58 (d, J=13.0 Hz, 1H), 1.72-1.84 (m, 6H), 1.93-2.02 (m, 2H), 2.43 (m, 1H), 3.01 (br. s., 2H), 4.28-4.36 (m, 1H), 7.40 (d, J=8.1 Hz, 1H), 7.51 (br. s., 2H), 7.74 (d, J=7.5 Hz, 1H), 11.18 (br. s., 2H).

2-(1-Methylpiperidin-4-yl)-3-oxo-2,3-dihydro-1H-indazole-4-carboxamide (I), cpd 8

$R_1$=1-methylpiperidin-4-yl; $R_2$=$R_3$=H $^1$H NMR (599.9 MHz, DMSO-$d_6$) δ ppm 1.79 (d, J=11.0 Hz, 2H), 1.96-2.06 (m, 2H), 2.12 (br. s., 2H), 2.26 (br. s., 3H), 2.95 (d, J=11.4 Hz, 2H), 4.28-4.35 (m, 1H), 7.43 (d, J=8.1 Hz, 1H), 7.55 (br. s., 2H), 7.78 (d, J=7.5 Hz, 1H), 10.97 (br. s., 1H) 11.09 (br. s., 1H).

2-(1-Cyclobutylpiperidin-4-yl)-3-oxo-2,3-dihydro-1H-indazole-4-carboxamide (I), cpd 16

$R_1$=1-cyclobutylpiperidin-4-yl; $R_2$=$R_3$=H $^1$H NMR (400.5 MHz, DMSO-$d_6$) δ ppm 1.60-2.08 (m, 12H) 2.83 (br. s., 1H) 2.97 (br. s., 2H) 4.35 (br. s., 1H) 7.45 (d, J=7.9 Hz, 1H) 7.59 (br. s., 2H) 7.82 (d, J=6.8 Hz, 1H) 11.04 (br. s., 2H).

2-(1-Cyclohexylpiperidin-4-yl)-6-fluoro-1-methyl-3-oxo-2,3-dihydro-1H-indazole-4-carboxamide (I), cpd 22

$R_1$=1-cyclohexylpiperidin-4-yl; $R_2$=methyl; $R_3$=F $^1$H NMR (599.9 MHz, DMSO-$d_6$) δ ppm 1.08 (m, 1H) 1.21 (br. s., 4H) 1.58 (d, J=11.7 Hz, 1H) 1.75 (br. s., 6H) 2.31 (br. s., 4H) 2.92 (br. s., 2H) 3.43 (s, 3H) 4.10 (br. s., 1H) 7.60 (dd, $J_{HF}$=10.6, $J_{HH}$=2.2 Hz, 1H) 7.72 (dd, $J_{HF}$=9.2, $J_{HH}$=2.2 Hz, 1H) 7.84 (br. s., 1H) 10.83 (br. s., 1H).

2-(1-Cyclohexylpiperidin-4-yl)-6-fluoro-3-oxo-2,3-dihydro-1H-indazole-4-carboxamide (I), cpd 23

$R_1$=1-cyclohexylpiperidin-4-yl; $R_2$=H; $R_3$=F $^1$H NMR (599.9 MHz, DMSO-$d_6$) δ ppm 1.06-1.14 (m, 1H) 1.20-1.29 (m, 2H) 1.29-1.39 (m, 2H) 1.60 (d, J=12.4 Hz, 1H) 1.80 (d, J=12.4 Hz, 2H) 1.85-1.97 (m, 3H) 2.11-2.21 (m, 2H) 2.85 (br. s., 2H) 3.30 (signal overlapped by water, 2H) 4.47 (br. s., 1H) 7.02 (br. s., 1H) 7.23 (br. s., 1H) 7.51 (br. s. 1H) 10.13 (br. s. 1H) 11.61 (br. s., 1H).

2-[1-(Cyclohexylmethyl)piperidin-4-yl]-3-oxo-2,3-dihydro-1H-indazole-4-carboxamide (I), cpd 31

$R_1$=1-(cyclohexylmethyl)piperidin-4-yl; $R_2$=$R_3$=H $^1$H NMR (400.5 MHz, DMSO-$d_6$) δ ppm 0.77-0.94 (m, 1H) 1.13-2.23 (m, 18H) 2.97 (br. s., 2H) 4.14-4.42 (m, 1H) 7.44 (d, J=8.2 Hz, 1H) 7.55-7.63 (m, 2H) 7.82 (d, J=7.0 Hz, 1H) 10.96 (br. s., 1H) 11.05 (br. s., 1H).

3-Oxo-2-[1-(thiophen-2-ylmethyl)piperidin-4-yl]-2,3-dihydro-1H-indazole-4-carboxamide (I), cpd 62

$R_1$=1-(thiophen-2-ylmethyl)piperidin-4-yl; $R_2$=$R_3$=H $^1$H NMR (400.5 MHz, DMSO-$d_6$) δ ppm 1.81 (d, J=12.4 Hz, 2H) 1.90-2.08 (m, 2H) 2.08-2.23 (m, 2H) 3.01 (d, J=11.5 Hz, 2H) 3.74 (s, 2H) 4.29-4.41 (m, 1H) 6.95-7.01 (m, 2H) 7.39-7.51 (m, 2H) 7.58 (br. s., 1H) 7.58-7.65 (m, 1H) 7.84 (d, J=7.3 Hz, 1H) 11.03 (br. s., 2H).

2-[1-(Cyclohex-3-en-1-ylmethyl)piperidin-4-yl]-3-oxo-2,3-dihydro-1H-indazole-4-carboxamide (I), cpd 64

$R_1$=1-(cyclohex-3-en-1-ylmethyl)piperidin-4-yl; $R_2$=$R_3$=H $^1$H NMR (400.5 MHz, DMSO-$d_6$) δ ppm 1.10-1.30 (m, 1H) 1.58-1.70 (m, 1H) 1.72-2.14 (m, 11H) 2.19-2.26 (m, 2H) 2.98 (br. s., 2H) 4.28-4.38 (m, 1H) 5.58-5.73 (m, 2H) 7.44 (d, J=8.3 Hz, 1H) 7.53-7.65 (m, 2H) 7.82 (d, J=7.4 Hz, 1H) 10.95 (br. s., 1H) 11.07 (br. s., 1H).

2-[1-(Furan-2-ylmethyl)piperidin-4-yl]-3-oxo-2,3-dihydro-1H-indazole-4-carboxamide (I), cpd 66

$R_1$=1-(furan-2-ylmethyl)piperidin-4-yl; $R_2$=$R_3$=H $^1$H NMR (400.5 MHz, DMSO-$d_6$) δ ppm 1.72-1.86 (m, 2H) 1.91-2.04 (m, 2H) 2.10-2.20 (m, 2H) 2.96 (d, J=11.6 Hz, 2H) 3.55 (s, 2H) 4.24-4.37 (m, 1H) 6.30 (d, J=3.2 Hz, 1H) 6.41 (dd, J=3.2, 1.8 Hz, 1H) 7.45 (d, J=7.9 Hz, 1H) 7.55-7.66 (m, 3H) 7.84 (d, J=7.3 Hz, 1H) 10.99 (br. s., 1H) 11.03 (br. s., 1H).

Conversion 3

2-[1-(4,4-Difluorocyclohexyl)piperidin-4-yl]-1-methyl-3-oxo-2,3-dihydro-1H-indazole-4-carboxamide (I), cpd 6

$R_1$=1-(4,4-difluorocyclohexyl)piperidin-4-yl; $R_2$=methyl; $R_3$=H

To a suspension of 2-[1-(4,4-difluorocyclohexyl)piperidin-4-yl]-3-oxo-2,3-dihydro-1H-indazole-4-carboxamide (166 mg, 0.44 mmol) in N,N-dimethylformamide (1 mL), methyl iodide (0.41 mL, 0.66 mmol) and potassium carbonate (61 mg, 0.44 mmol) were added. The resulting mixture was stirred at 80° C. for 8 hours and diluted with ethyl acetate. Organic layer was washed with 10% aqueous ammonia solution, dried over sodium sulphate and evaporated. The crude was purified by flash chromatography (dichloromethane/methanol 95:5) to give the title compound (89 mg, 52%).

$^1$H NMR (599.9 MHz, DMSO-$d_6$) δ ppm 1.49-1.59 (m, 2H), 1.71-1.80 (m, 4H), 1.82-1.89 (m, 2H), 2.00-2.09 (m, 2H), 2.25-2.32 (m, 2H), 2.35-2.39 (m, 2H), 2.54 (signal overlapped by DMSO, 1H), 2.92-2.98 (m, 2H), 3.40 (s, 3H), 4.09-4.19 (m, 1H), 7.65 (br. s., 1H), 7.70 (dd, J=8.0, 7.3 Hz, 1H), 7.72 (d, J=8.0 Hz, 1H), 7.91 (d, J=7.3 Hz, 1H), 10.80 (br. s., 1H).

Operating in an analogous way, but employing suitable substituted starting material, the following compounds were obtained:

2-(1-Cyclohexylpiperidin-4-yl)-1-methyl-3-oxo-2,3-dihydro-1H-indazole-4-carboxamide (I), cpd 5

$R_1$=1-cyclohexylpiperidin-4-yl; $R_2$=methyl; $R_3$=H $^1$H NMR (599.9 MHz, DMSO-$d_6$) δ ppm 1.04-1.13 (m, 1H), 1.17-1.27 (m, 4H), 1.58 (d, J=12.4 Hz, 1H), 1.68-1.81 (m, 6H), 2.25-2.40 (m, 5H), 2.93 (br. s., 2H), 3.40 (s, 3H), 4.12 (br. s., 1H), 7.65 (br. s., 1H), 7.69-7.71 (m, 1H), 7.73-7.74 (m, 1H), 7.91 (dd, J=7.2, 1.0 Hz, 1H), 10.81 (br. s., 1H).

2-(1-Cyclopentylpiperidin-4-yl)-1-methyl-3-oxo-2,3-dihydro-1H-indazole-4-carboxamide (I), cpd 7

$R_1$=1-cyclopentylpiperidin-4-yl; $R_2$=methyl; $R_3$=H $^1$H NMR (599.9 MHz, DMSO-$d_6$) δ ppm 1.30-1.39 (m, 2H), 1.46-1.54 (m, 2H), 1.58-1.64 (m, 2H), 1.69-1.84 (m, 4H), 1.99-2.09 (m, 2H), 2.31-2.44 (m, 2H), 2.54 (signal overlapped by DMSO, 1H), 3.05 (d, J=10.2 Hz, 2H), 3.40 (s, 3H), 4.12-4.20 (m, 1H), 7.65 (br. s., 1H), 7.68-7.71 (m, 1H), 7.73-7.75 (m, 1H), 7.91 (dd, J=7.3, 0.9 Hz, 1H), 10.80 (br. s., 1H).

1-Methyl-3-oxo-2-(piperidin-4-yl)-2,3-dihydro-1H-indazole-4-carboxamide (I), cpd 9

$R_1$=piperidin-4-yl; $R_2$=methyl; $R_3$=H $^1$H NMR (599.9 MHz, DMSO-$d_6$) δ ppm 1.95 (d, J=12.4 Hz, 2H), 2.57-2.68 (m, 2H), 2.96-3.12 (m, 2H), 3.42 (signal overlapped by water, 2H), 3.47 (signal overlapped by water, 3H) 4.51-4.55 (m, 1H), 7.70 (br. s., 1H), 7.72-7.75 (m, 1H), 7.75-7.78 (m, 1H), 7.93 (dd, J=7.1, 1.3 Hz, 1H), 8.62 (br. s., 1H), 8.85 (br. s., 1H), 10.66 (br. s., 1H).

1-Methyl-3-oxo-2-[1-(propan-2-yl)piperidin-4-yl]-2,3-dihydro-1H-indazole-4-carboxamide (I), cpd 14

$R_1$=1-(propan-2-yl)piperidin-4-yl; $R_2$=methyl; $R_3$=H $^1$H NMR (599.9 MHz, DMSO-$d_6$) δ ppm 0.99 (d, J=6.6 Hz, 6H), 1.74 (d, J=12.4 Hz, 2H), 2.19-2.28 (m, 2H), 2.29-2.38 (m, 2H), 2.70-2.78 (m, 1H), 2.90 (d, J=10.5 Hz, 2H), 3.40 (s, 3H), 4.09-4.17 (m, 1H), 7.65 (br. s., 1H), 7.68-7.72 (m, 1H), 7.72-7.75 (m, 1H), 7.91 (dd, J=7.1, 0.9 Hz, 1H), 10.82 (br. s., 1H).

2-(1-Cyclobutylpiperidin-4-yl)-1-methyl-3-oxo-2,3-dihydro-1H-indazole-4-carboxamide (I), cpd 18

$R_1$=1-cyclobutylpiperidin-4-yl; $R_2$=methyl; $R_3$=H $^1$H NMR (400.5 MHz, DMSO-$d_6$) δ ppm 1.57-1.86 (m, 8H) 1.88-2.04 (m, 2H) 2.27-2.41 (m, 2H) 2.69-2.76 (m, 1H) 2.90 (d, J=12.0 Hz, 2H) 3.40 (s, 3H) 4.09-4.20 (m, 1H) 7.65 (br. s., 1H) 7.67-7.72 (m, 1H) 7.73-7.76 (m, 1H) 7.91 (dd, J=7.1, 1.3 Hz, 1H) 10.80 (br. s., 1H).

2-[1-(Cyclohexylmethyl)piperidin-4-yl]-1-methyl-3-oxo-2,3-dihydro-1H-indazole-4-carboxamide (I), cpd 33

$R_1$=1-(cyclohexylmethyl)piperidin-4-yl; $R_2$=methyl; $R_3$=H $^1$H NMR (400.5 MHz, DMSO-$d_6$) δ ppm 0.78-2.41 (m, 19H) 2.88-2.97 (m, 2H) 4.06-4.22 (m, 1H) 7.65 (br. s., 1H) 7.67-7.78 (m, 2H) 7.91 (dd, J=7.1, 1.5 Hz, 1H) 10.79 (br. s., 1H).

1-Methyl-3-oxo-2-[1-(thiophen-2-ylmethyl)piperidin-4-yl]-2,3-dihydro-1H-indazole-4-carboxamide (I), cpd 63

$R_1$=1-(thiophen-2-ylmethyl)piperidin-4-yl; $R_2$=methyl; $R_3$=H $^1$H NMR (400.5 MHz, DMSO-$d_6$) δ ppm 1.74 (m, 2H) 2.06-2.18 (m, 2H) 2.35-2.46 (m, 2H) 2.99 (d, J=10.2 Hz, 2H) 3.40 (s, 3H) 3.74 (s, 2H) 4.10-4.21 (m, 1H) 6.95-7.01 (m, 2H) 7.44 (dd, J=4.3, 1.8 Hz, 1H) 7.66 (br. s., 1H) 7.67-7.72 (m, 1H) 7.72-7.75 (m, 1H) 7.91 (dd, J=7.0, 1.5 Hz, 1H) 10.79 (br. s., 1H).

2-[1-(Cyclohex-3-en-1-ylmethyl)piperidin-4-yl]-1-methyl-3-oxo-2,3-dihydro-1H-indazole-4-carboxamide (I), cpd $R_1$=1-(cyclohex-3-en-1-ylmethyl)piperidin-4-yl; $R_2$=methyl; $R_3$=H $^1$H NMR (599.9 MHz, DMSO-$d_6$) δ ppm 1.09-2.41 (m, 13H) 2.34-2.44 (m, 2H) 2.95 (br. s., 2H) 3.40 (s, 3H) 4.14 (br. s., 1H) 5.62-5.70 (s, 2H) 7.66 (br. s., 1H) 7.68-7.72 (m, 1H) 7.73-7.75 (m, 1H) 7.91 (dd, J=7.1, 1.3 Hz, 1H) 10.80 (br. s., 1H).

2-[1-(Furan-2-ylmethyl)piperidin-4-yl]-1-methyl-3-oxo-2,3-dihydro-1H-indazole-4-carboxamide (I), cpd 67

$R_1$=1-(furan-2-ylmethyl)piperidin-4-yl; $R_2$=methyl; $R_3$=H $^1$H NMR (400.5 MHz, DMSO-$d_6$) δ ppm 1.72 (d, J=12.0 Hz, 2H) 2.08-2.16 (m, 2H) 2.34-2.44 (m, 2H) 2.94 (d, J=11.3 Hz, 2H) 3.39 (s, 3H) 3.54 (s, 2H) 4.07-4.20 (m, 1H) 6.30 (d, J=3.0 Hz, 1H) 6.41 (dd, J=3.0, 1.8 Hz, 1H) 7.59 (dd, J=1.8, 0.8 Hz, 1H) 7.65 (br. s., 1H) 7.67-7.71 (m, 1H) 7.72-7.75 (m, 1H) 7.91 (dd, J=7.0, 1.3 Hz, 1H) 10.79 (br. s., 1H).

Tert-butyl 4-(4-carbamoyl-6-fluoro-1-methyl-3-oxo-1,3-dihydro-2H-indazol-2-yl)piperidine-1-carboxylate (I)

$R_1$=1-(tert-butoxycarbonyl)piperidin-4-yl; $R_2$=methyl; $R_3$=F $^1$H NMR (599.9 MHz, DMSO-$d_6$) δ ppm 1.42 (s, 9H) 1.76 (d, J=12.4, 2H) 2.19-2.28 (m, 2H) 2.85 (br. s., 2H) 3.43 (s, 3H) 4.08 (br. s., 2H) 4.32-4.37 (m, 1H) 7.60 (dd, J=10.8, 2.2 Hz, 1H) 7.73 (dd, J=9.2, 2.2 Hz, 1H) 7.85 (br. s., 1H) 10.75 (s, 1H).

The invention claimed is:
1. A compound of formula (I):

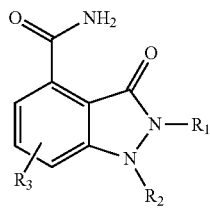

wherein
$R_1$ is an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl and heteroaryl;
$R_2$ is hydrogen, $COR_4$ or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl and heteroaryl;
$R_3$ is hydrogen, halogen, cyano, nitro, $NHCOR_4$, $COR_4$, $NR_5R_6$, $NR_5COR_4$, $OR_7$, $SR_7$, $SOR_{10}$, $SO_2R_{10}$, $NHSOR_{10}$, $NHSO_2R_{10}$, or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl;
$R_4$ is hydrogen, $NR_5R_7$, $OR_7$, $SR_7$, or an optionally substituted group selected from linear or branched $C_1$-$C_6$ alkyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl;
$R_5$ and $R_6$ are independently hydrogen, or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl, or $R_5$ and $R_6$, taken together with the nitrogen to which they are bonded, form an optionally substituted heterocyclyl group;
$R_7$ is hydrogen, $COR_5$, $SOR_{10}$, $SO_2R_{10}$ or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl, $R_8O$—$C_1$-$C_6$ alkyl, heterocyclyl-$C_1$-$C_6$ alkyl, aryl-$C_1$-$C_6$ alkyl and heteroaryl-$C_1$-$C_6$ alkyl, wherein $R_5$ is as defined above;
$R_8$ and $R_9$ are independently hydrogen, $COR_4$ or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl and heteroaryl, or $R_8$ and $R_9$, taken together with the nitrogen to which they are bonded, form an optionally substituted heterocyclyl group, wherein $R_4$ is as defined above;
$R_{10}$ is hydrogen, $NR_5R_6$, $OR_7$ or an optionally substituted group selected from linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, heteroaryl, $R_8R_9N$—$C_1$-$C_6$ alkyl and $R_8O$—$C_1$-$C_6$ alkyl, wherein $R_5$, $R_6$, $R_7$, $R_8$ and $R_9$ are as defined above;
or a pharmaceutically acceptable salt thereof.
2. A compound of formula (I) according to claim 1, characterized in that
$R_1$ is an optionally substituted group selected from linear or branched $C_1$-$C_6$ alkyl, $C_3$-$C_7$ cycloalkyl, heterocyclyl, aryl and heteroaryl, the optional substituents being one or more halogen, cyano, $NHCOR_4$, $COR_4$, $NR_5R_6$, $NR_5COR_4$, $OR_7$, oxo (=O) or an optionally substituted group selected from linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl, heteroaryl-$C_1$-$C_6$ alkyl, $R_8R_9N$—$C_1$-$C_6$ alkyl and $R_8O$—$C_1$-$C_6$ alkyl, the optional further substituents being one or more halogen, $NHCOR_4$, $NR_5R_6$, $NR_5COR_4$, $OR_7$, oxo (=O), $SR_7$, or an optionally substituted group selected from linear or branched $C_1$-$C_6$ alkyl, aryl, heterocyclyl, $R_8R_9N$—$C_1$-$C_6$ alkyl and $R_8O$—$C_1$-$C_6$ alkyl.
3. A compound of formula (I) according to claim 1, wherein $R_1$ is an optionally substituted group selected from $C_3$-$C_7$ cycloalkyl, heterocyclyl, aryl and heteroaryl, the optional substituents being one or more halogen, cyano, $NHCOR_4$, $COR_4$, $NR_5R_6$, $NR_5COR_4$, $OR_7$, oxo (=O) or an optionally substituted group selected from linear or branched $C_1$-$C_6$ alkyl, $C_3$-$C_7$ cycloalkyl, heterocyclyl, aryl, heteroaryl, $C_3$-$C_7$ cycloalkyl-$C_1$-$C_6$ alkyl, heterocyclyl-$C_1$-$C_6$ alkyl, aryl-$C_1$-$C_6$ alkyl, heteroaryl-$C_1$-$C_6$ alkyl, $R_8R_9N$—$C_1$-$C_6$ alkyl and $R_8O$—$C_1$-$C_6$ alkyl, the optional further substituents being one or more halogen, $NHCOR_4$, $NR_5R_6$, $NR_5COR_4$, $OR_7$, oxo (=O), $SR_7$ or an optionally substituted group selected from linear or branched $C_1$-$C_6$ alkyl, aryl, heterocyclyl, $R_8R_9N$—$C_1$-$C_6$ alkyl and $R_8O$—$C_1$-$C_6$ alkyl; and
$R_2$ is hydrogen, $COR_4$ or an optionally substituted group selected from linear or branched $C_1$-$C_6$ alkyl, $C_3$-$C_7$ cycloalkyl, heterocyclyl, aryl and heteroaryl.
4. A compound of formula (I) according to claim 1, wherein
$R_2$ is hydrogen or an optionally substituted group selected from linear or branched $C_1$-$C_6$ alkyl, $C_3$-$C_7$ cycloalkyl, heterocyclyl, aryl and heteroaryl; and
$R_3$ is hydrogen, halogen, cyano, nitro, $NHCOR_4$, $NR_5R_6$, $NR_5COR_4$, $OR_7$, or an optionally substituted group selected from linear or branched $C_1$-$C_6$ alkyl, $R_8R_9N$—$C_1$-$C_6$ alkyl and $R_8O$—$C_1$-$C_6$ alkyl.
5. A compound of formula (I) according to claim 1, wherein $R_3$ is hydrogen, halogen, $NHCOR_4$, $NR_5R_6$, NR$_5$COR$_4$, OR, or an optionally substituted group selected from linear or branched C$_1$-C$_6$ alkyl, R$_8$R$_9$N—C$_1$-C$_6$ alkyl and R$_8$O—C$_1$-C$_6$ alkyl.

6. A compound of formula (I) according to claim 1, wherein R$_1$ is an optionally substituted group selected from heterocyclyl, aryl and heteroaryl, the optional substituents being, one or more COR$_4$ or an optionally further substituted group selected from linear or branched C$_1$-C$_6$ alkyl, C$_3$-C$_7$ cycloalkyl, heterocyclyl, aryl, heteroaryl, C$_3$-C$_7$ cycloalkyl-C$_1$-C$_6$ alkyl, heterocyclyl-C$_1$-C$_6$ alkyl, aryl-C$_1$-C$_6$ alkyl and heteroaryl-C$_1$-C$_6$ alkyl, the optional further substituents being one or more halogen, OR$_7$, oxo (=O) or an optionally substituted group selected from C$_1$-C$_6$ alkyl, aryl, heterocyclyl and R$_8$O—C$_1$-C$_6$ alkyl;
  R$_2$ is hydrogen or a C$_1$-C$_6$ alkyl group;
  R$_3$ is hydrogen or halogen;
  R$_4$ is OR$_7$;
  R$_7$ is hydrogen, optionally substituted C$_1$-C$_6$ alkyl or aryl-C$_1$-C$_6$ alkyl group, substituents being one or more halogen; and
  R$_8$ is hydrogen.

7. A compound of formula (I) according to claim 1, wherein R$_1$ is an optionally substituted piperidinyl or phenyl group, the optional substituents being, one or more, COR$_4$ or an optionally further substituted group selected from methyl, ethyl, propyl, cyclohexyl, cyclopentyl, cyclobutyl, morpholinyl, piperazinyl, pyrazolyl, cyclohexyl-methyl, cyclohexenyl-methyl, piperidinyl-methyl, benzyl, pyridyl-methyl, pyrrolyl-methyl, pyrazolyl-methyl, imidazolyl-methyl, thienyl-methyl, indolyl-methyl, thiazolyl-methyl and furyl-methyl, the optional further substituents being one or more bromine, fluorine, chlorine, isopropyl, methyl, phenyl, morpholinyl, piperidinyl, hydroxy-methyl, OR$_7$, or oxo (=O);
  R$_2$ is hydrogen or a methyl group;
  R$_3$ is hydrogen or fluorine;
  R$_4$ is OR$_7$; and
  R$_7$ is hydrogen, an optionally substituted methyl, tert-butyl or benzyl group, the substituents being one or more fluorine.

8. A compound of formula (I) or a salt thereof, selected from the group consisting of:
  3-oxo-2-(piperidin-4-yl)-2,3-dihydro-1H-indazole-4-carboxamide,
  2-(1-cyclopentylpiperidin-4-yl)-3-oxo-2,3-dihydro-1H-indazole-4-carboxamide,
  2-(1-cyclohexylpiperidin-4-yl)-3-oxo-2,3-dihydro-1H-indazole-4-carboxamide,
  2-[1-(4,4-difluorocyclohexyl)piperidin-4-yl]-3-oxo-2,3-dihydro-1H-indazole-4-carboxamide,
  2-(1-cyclohexylpiperidin-4-yl)-1-methyl-3-oxo-2,3-dihydro-1H-indazole-4-carboxamide,
  2-[1-(4,4-difluorocyclohexyl)piperidin-4-yl]-1-methyl-3-oxo-2,3-dihydro-1H-indazole-4-carboxamide,
  2-(1-cyclopentylpiperidin-4-yl)-1-methyl-3-oxo-2,3-dihydro-1H-indazole-4-carboxamide,
  2-(1-methylpiperidin-4-yl)-3-oxo-2,3-dihydro-1H-indazole-4-carboxamide,
  1-methyl-3-oxo-2-(piperidin-4-yl)-2,3-dihydro-1H-indazole-4-carboxamide,
  1-methyl-2-(1-methylpiperidin-4-yl)-3-oxo-2,3-dihydro-1H-indazole-4-carboxamide,
  2-(1-ethylpiperidin-4-yl)-3-oxo-2,3-dihydro-1H-indazole-4-carboxamide,
  3-oxo-2-(1-propylpiperidin-4-yl)-2,3-dihydro-1H-indazole-4-carboxamide,
  2-(1-ethylpiperidin-4-yl)-1-methyl-3-oxo-2,3-dihydro-1H-indazole-4-carboxamide,
  1-methyl-3-oxo-2-[1-(propan-2-yl)piperidin-4-yl]-2,3-dihydro-1H-indazole-4-carboxamide,
  3-oxo-2-[1-(propan-2-yl)piperidin-4-yl]-2,3-dihydro-1H-indazole-4-carboxamide,
  2-(1-cyclobutylpiperidin-4-yl)-3-oxo-2,3-dihydro-1H-indazole-4-carboxamide,
  2-(1-cyclobutylpiperidin-4-yl)-6-fluoro-3-oxo-2,3-dihydro-1H-indazole-4-carboxamide,
  2-(1-cyclobutylpiperidin-4-yl)-1-methyl-3-oxo-2,3-dihydro-1H-indazole-4-carboxamide,
  2-(1-cyclobutylpiperidin-4-yl)-6-fluoro-1-methyl-3-oxo-2,3-dihydro-1H-indazole-4-carboxamide,
  6-fluoro-3-oxo-2-(piperidin-4-yl)-2,3-dihydro-1H-indazole-4-carboxamide,
  6-fluoro-1-methyl-3-oxo-2-(piperidin-4-yl)-2,3-dihydro-1H-indazole-4-carboxamide,
  2-(1-cyclohexylpiperidin-4-yl)-6-fluoro-1-methyl-3-oxo-2,3-dihydro-1H-indazole-4-carboxamide,
  2-(1-cyclohexylpiperidin-4-yl)-6-fluoro-3-oxo-2,3-dihydro-1H-indazole-4-carboxamide,
  2-[1-(4,4-difluorocyclohexyl)piperidin-4-yl]-6-fluoro-1-methyl-3-oxo-2,3-dihydro-1H-indazole-4-carboxamide,
  2-[1-(4,4-dichlorocyclohexyl)piperidin-4-yl]-1-methyl-3-oxo-2,3-dihydro-1H-indazole-4-carboxamide,
  6-chloro-2-(1-cyclohexylpiperidin-4-yl)-1-methyl-3-oxo-2,3-dihydro-1H-indazole-4-carboxamide,
  2-(1-cyclohexylazetidin-3-yl)-3-oxo-2,3-dihydro-1H-indazole-4-carboxamide,
  2-(1-cyclohexylazetidin-3-yl)-1-methyl-3-oxo-2,3-dihydro-1H-indazole-4-carboxamide,
  6-chloro-2-(1-cyclohexylpiperidin-4-yl)-3-oxo-2,3-dihydro-1H-indazole-4-carboxamide,
  2-(1-cyclohexylazetidin-3-yl)-6-fluoro-1-methyl-3-oxo-2,3-dihydro-1H-indazole-4-carboxamide,
  2-[1-(cyclohexylmethyl)piperidin-4-yl]-3-oxo-2,3-dihydro-1H-indazole-4-carboxamide,
  2-(1-benzylpiperidin-4-yl)-3-oxo-2,3-dihydro-1H-indazole-4-carboxamide,
  2-[1-(cyclohexylmethyl)piperidin-4-yl]-1-methyl-3-oxo-2,3-dihydro-1H-indazole-4-carboxamide,
  2-(1-benzylpiperidin-4-yl)-1-methyl-3-oxo-2,3-dihydro-1H-indazole-4-carboxamide,
  3-oxo-2-(1-phenylpiperidin-4-yl)-2,3-dihydro-1H-indazole-4-carboxamide,
  1-methyl-3-oxo-2-(1-phenylpiperidin-4-yl)-2,3-dihydro-1H-indazole-4-carboxamide,
  6-fluoro-1-methyl-3-oxo-2-[4-(piperidin-4-yl)phenyl]-2,3-dihydro-1H-indazole-4-carboxamide,
  3-oxo-2-[4-(piperidin-4-yl)phenyl]-2,3-dihydro-1H-indazole-4-carboxamide,
  1-methyl-3-oxo-2-[4-(piperidin-4-yl)phenyl]-2,3-dihydro-1H-indazole-4-carboxamide,
  6-fluoro-1-methyl-3-oxo-2-(1-phenylpiperidin-4-yl)-2,3-dihydro-1H-indazole-4-carboxamide,
  3-oxo-2-[1-(thiophen-3-ylmethyl)piperidin-4-yl]-2,3-dihydro-1H-indazole-4-carboxamide,
  3-oxo-2-[1-(1H-pyrrol-3-ylmethyl)piperidin-4-yl]-2,3-dihydro-1H-indazole-4-carboxamide,
  6-fluoro-1-methyl-3-oxo-2-[1-(thiophen-3-ylmethyl)piperidin-4-yl]-2,3-dihydro-1H-indazole-4-carboxamide, 1-methyl-3-oxo-2-[1-(1H-pyrrol-3-ylmethyl)piperidin-4-yl]-2,3-dihydro-1H-indazole-4-carboxamide,
2-[1-(furan-3-ylmethyl)piperidin-4-yl]-1-methyl-3-oxo-2,3-dihydro-1H-indazole-4-carboxamide,
3-oxo-2-[1-(pyridin-4-yl)piperidin-4-yl]-2,3-dihydro-1H-indazole-4-carboxamide,
2-[1-(furan-3-ylmethyl)piperidin-4-yl]-3-oxo-2,3-dihydro-1H-indazole-4-carboxamide,
1-methyl-3-oxo-2-[1-(1H-pyrrol-2-ylmethyl)piperidin-4-yl]-2,3-dihydro-1H-indazole-4-carboxamide,
3-oxo-2-[1-(pyridin-3-yl)piperidin-4-yl]-2,3-dihydro-1H-indazole-4-carboxamide,
1-methyl-3-oxo-2-[1-(pyridin-4-yl)piperidin-4-yl]-2,3-dihydro-1H-indazole-4-carboxamide,
1-methyl-3-oxo-2-[1-(pyridin-3-yl)piperidin-4-yl]-2,3-dihydro-1H-indazole-4-carboxamide,
6-fluoro-1-methyl-3-oxo-2-[1-(pyridin-4-yl)piperidin-4-yl]-2,3-dihydro-1H-indazole-4-carboxamide,
6-fluoro-1-methyl-3-oxo-2-[1-(pyridin-3-yl)piperidin-4-yl]-2,3-dihydro-1H-indazole-4-carboxamide,
3-oxo-2-[4-(pyridin-4-yl)phenyl]-2,3-dihydro-1H-indazole-4-carboxamide,
1-ethyl-3-oxo-2-(piperidin-4-yl)-2,3-dihydro-1H-indazole-4-carboxamide,
2-(1-cyclohexylpiperidin-4-yl)-1-ethyl-3-oxo-2,3-dihydro-1H-indazole-4-carboxamide,
1-methyl-3-oxo-2-[4-(pyridin-4-yl)phenyl]-2,3-dihydro-1H-indazole-4-carboxamide,
1-ethyl-6-fluoro-3-oxo-2-(piperidin-4-yl)-2,3-dihydro-1H-indazole-4-carboxamide,
3-oxo-2-[4-(pyridin-3-yl)phenyl]-2,3-dihydro-1H-indazole-4-carboxamide,
6-fluoro-3-oxo-2-[4-(pyridin-3-yl)phenyl]-2,3-dihydro-1H-indazole-4-carboxamide,
6-fluoro-1-methyl-3-oxo-2-[4-(pyridin-3-yl)phenyl]-2,3-dihydro-1H-indazole-4-carboxamide,
3-oxo-2-[1-(thiophen-2-ylmethyl)piperidin-4-yl]-2,3-dihydro-1H-indazole-4-carboxamide,
1-methyl-3-oxo-2-[1-(thiophen-2-ylmethyl)piperidin-4-yl]-2,3-dihydro-1H-indazole-4-carboxamide,
2-[1-(cyclohex-3-en-1-ylmethyl)piperidin-4-yl]-3-oxo-2,3-dihydro-1H-indazole-4-carboxamide,
2-[1-(cyclohex-3-en-1-ylmethyl)piperidin-4-yl]-1-methyl-3-oxo-2,3-dihydro-1H-indazole-4-carboxamide,
2-[1-(furan-2-ylmethyl)piperidin-4-yl]-3-oxo-2,3-dihydro-1H-indazole-4-carboxamide, and
2-[1-(furan-2-ylmethyl)piperidin-4-yl]-1-methyl-3-oxo-2,3-dihydro-1H-indazole-4-carboxamide.

9. A process for the preparation of a compound of formula (I) as defined in claim 1, which process comprises one of the following steps:

Step a) halogenating a compound of formula (VII):

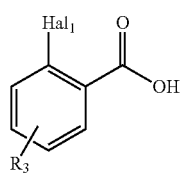

VII wherein $Hal_1$ is halogen such as Cl, Br, I and $R_3$ is as defined in claim 1;

Step b) coupling the resultant compound of formula (VI):

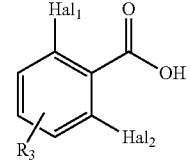

VI wherein $Hal_2$ is halogen such as Cl, Br, I, different from $Hal_1$, and $R_3$ and $Hal_1$ are as defined above with a suitable hydrazine (IX):

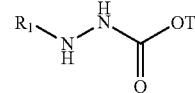

IX wherein T is linear or branched $C_1$-$C_6$ alkyl or aryl $C_1$-$C_6$ alkyl group and $R_1$ is as defined in claim 1;

Step c) cyclizing the resultant compound of formula (V):

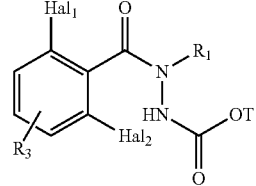

V wherein $Hal_1$, $Hal_2$, T, $R_1$ and $R_3$ are as defined above;
either
Step d) cyano-de-halogenating the resultant compound of formula (IV):

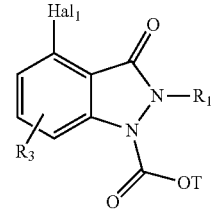

IV wherein $Hal_1$, T, $R_1$ and $R_3$ are as defined above;
or
Step f) first, removing the nitrogen protecting group of a compound of formula (IV) as defined above;
Step d') then cyano-de-halogenating the resultant compound of formula (X):

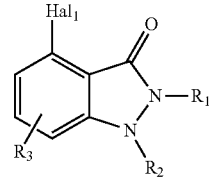

X wherein $R_2$ is hydrogen and $Hal_1$, $R_1$, and $R_3$ are as defined above;
either
Step e) first hydrolyzing the compound of formula (III) obtained in step d):

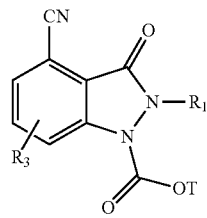

III wherein T, $R_1$ and $R_3$ are as defined above;
Step f) then removing the nitrogen protecting group of the resultant compound of formula (I):

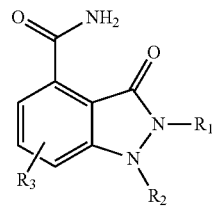

I wherein $R_2$ is $COR_4$, wherein $R_4$ is $OR_7$ and $R_7$ is linear or branched $C_1$-$C_6$ alkyl or aryl-$C_1$-$C_6$ alkyl; and $R_1$ and $R_3$ are as defined above, to give the corresponding compound of formula (I) wherein $R_2$ is hydrogen, and $R_1$ and $R_3$ are as defined above;
or
Step f') first, removing nitrogen protecting group of a compound of formula (III) obtained in step d);
Step e') then hydrolyzing the resultant compound of formula (VIII):

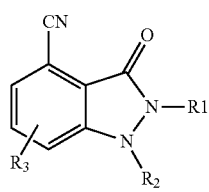

VIII wherein $R_2$ is hydrogen and $R_1$ and $R_3$ are as defined above, to give a compound of formula (I) wherein $R_2$ is hydrogen and $R_1$ and $R_3$ are as defined above;
optionally converting a compound of formula (I) into a different compound of formula (I) by known chemical reactions; and/or, if desired, converting a compound of formula (I) into a pharmaceutically acceptable salt thereof or converting a salt into a free compound of formula (I).

10. A method for treating diseases mediated by PARP-1 protein which comprises administering to a mammal in need thereof an effective amount of a compound of formula (I), as defined in claim 1, wherein the disease is selected from the group consisting of cancer, cardiovascular diseases, nervous system injury and inflammation.

11. The method according to claim 10 wherein the cancer is carcinomas, bladder, breast, colon, kidney, liver, lung, small cell lung cancer, esophagus, gall-bladder, ovary, pancreas, stomach, cervix, thyroid, prostate, skin, and squamous cell carcinoma; hematopoietic tumors of lymphoid lineage, leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, acute and chronic myelogenous leukemias, myelodysplastic syndrome and promyelocytic leukemia; tumors of mesenchymal origin, fibrosarcoma and rhabdomyosarcoma; tumors of the central and peripheral nervous system, astrocytoma neuroblastoma, glioma and schwannomas; melanoma, seminoma, teratocarcinoma, osteosarcoma, xeroderma pigmentosum, keratoxanthoma, thyroid follicular cancer and Kaposi's sarcoma.

12. The method according to claim 11 which provides tumor angiogenesis and metastasis inhibition.

13. The method according to claim 10 wherein the mammal in need thereof is a human.

14. An in vitro method for selectively inhibiting PARP-1 protein activity which comprises contacting the said protein with an effective amount of a compound of formula (I) as defined in claim 1.

15. A pharmaceutical composition comprising a therapeutically effective amount of a compound of formula (I) or a pharmaceutically acceptable salt thereof, as defined in claim 1, and at least one pharmaceutically acceptable excipient, carrier or diluent.

16. A pharmaceutical composition according to claim 15 further comprising one or more chemotherapeutic agents.

17. The pharmaceutical composition according to claim 16, wherein the chemotherapeutic agent is an alkylating agent.

18. The pharmaceutical composition according to claim 17, wherein the alkylating agent is temozolomide.

19. A product comprising a compound of formula (I) or a pharmaceutically acceptable salt thereof, as defined in claim 1, and one or more chemotherapeutic agents, as a combined preparation for simultaneous, separate or sequential use in anticancer therapy.

20. A product according to claim 19, wherein the chemotherapeutic agent is an alkylating agent.

21. A product according to claim 20, wherein the alkylating agent is temozolomide.

* * * * *